(12) United States Patent
Pizzi et al.

(10) Patent No.: US 11,732,228 B2
(45) Date of Patent: Aug. 22, 2023

(54) DEVICE FOR MULTI-WELL CELL-CULTURE PLATES, AND CORRESPONDING KIT

(71) Applicant: ELTEK S.p.A., Casale Monferrato (IT)

(72) Inventors: Marco Pizzi, Casale Monferrato (IT); Ilze Aulika, Casale Monferrato (IT)

(73) Assignee: ELTEK S.p.A., Casale Monferrato (IT)

( * ) Notice: Subject to any disclaimer, the term of this patent is extended or adjusted under 35 U.S.C. 154(b) by 493 days.

(21) Appl. No.: 16/628,449

(22) PCT Filed: Jul. 2, 2018

(86) PCT No.: PCT/IB2018/054911
§ 371 (c)(1),
(2) Date: Jan. 3, 2020

(87) PCT Pub. No.: WO2019/008505
PCT Pub. Date: Jan. 10, 2019

(65) Prior Publication Data
US 2020/0216789 A1    Jul. 9, 2020

(30) Foreign Application Priority Data

Jul. 5, 2017   (IT) .................... 102017000075491

(51) Int. Cl.
*B01L 3/00* (2006.01)
*C12M 1/00* (2006.01)
*C12M 1/32* (2006.01)

(52) U.S. Cl.
CPC ......... *C12M 23/12* (2013.01); *B01L 3/50853* (2013.01); *C12M 23/34* (2013.01);
(Continued)

(58) Field of Classification Search
CPC ...... C12M 23/12; C12M 23/34; C12M 23/38; B01L 3/50853; B01L 2300/046;
(Continued)

(56) References Cited

U.S. PATENT DOCUMENTS 4,599,315 A    7/1986  Terasaki et al.
6,776,964 B1   8/2004  Wijnschenk et al.
(Continued)

FOREIGN PATENT DOCUMENTS

EP    0 285 496    10/1988

OTHER PUBLICATIONS

International Search Report and Written Opinion of the ISA for PCT/IB2018/054911 dated Oct. 5, 2018, 12 pages.

*Primary Examiner* — Liban M Hassan
(74) *Attorney, Agent, or Firm* — Nixon & Vanderhye P.C.

(57) ABSTRACT

A device (20) for creating cell-exclusion zones comprises a baseplate (21) having a first major face from which a plurality of exclusion reliefs (22) project, each exclusion relief (22) having at least one distal end (23) configured for contact with a bottom (11b) of a respective well (11) of a multi-well cell-culture plate (10). The baseplate (21) and the plurality of exclusion reliefs (22) are defined at least in part by an elastic or flexible material in such a way that at least the baseplate (21) is elastically deformable at least during removal thereof from a multi-well cell-culture plate (10), the elastic or flexible material preferably being an elastomer.

11 Claims, 27 Drawing Sheets

(52) U.S. Cl.
CPC ........ *C12M 23/38* (2013.01); *B01L 2300/046* (2013.01); *B01L 2300/0829* (2013.01); *B01L 2300/0851* (2013.01); *B01L 2300/123* (2013.01)

(58) Field of Classification Search
CPC ..... B01L 2300/0829; B01L 2300/0851; B01L 2300/123
See application file for complete search history.

(56) References Cited

U.S. PATENT DOCUMENTS

| | | |
|---|---|---|
| 2008/0160539 A1 | 7/2008 | Murphy et al. |
| 2008/0194017 A1* | 8/2008 | Esser ................. C12M 23/12 435/307.1 |
| 2013/0281323 A1 | 10/2013 | Tran |

* cited by examiner

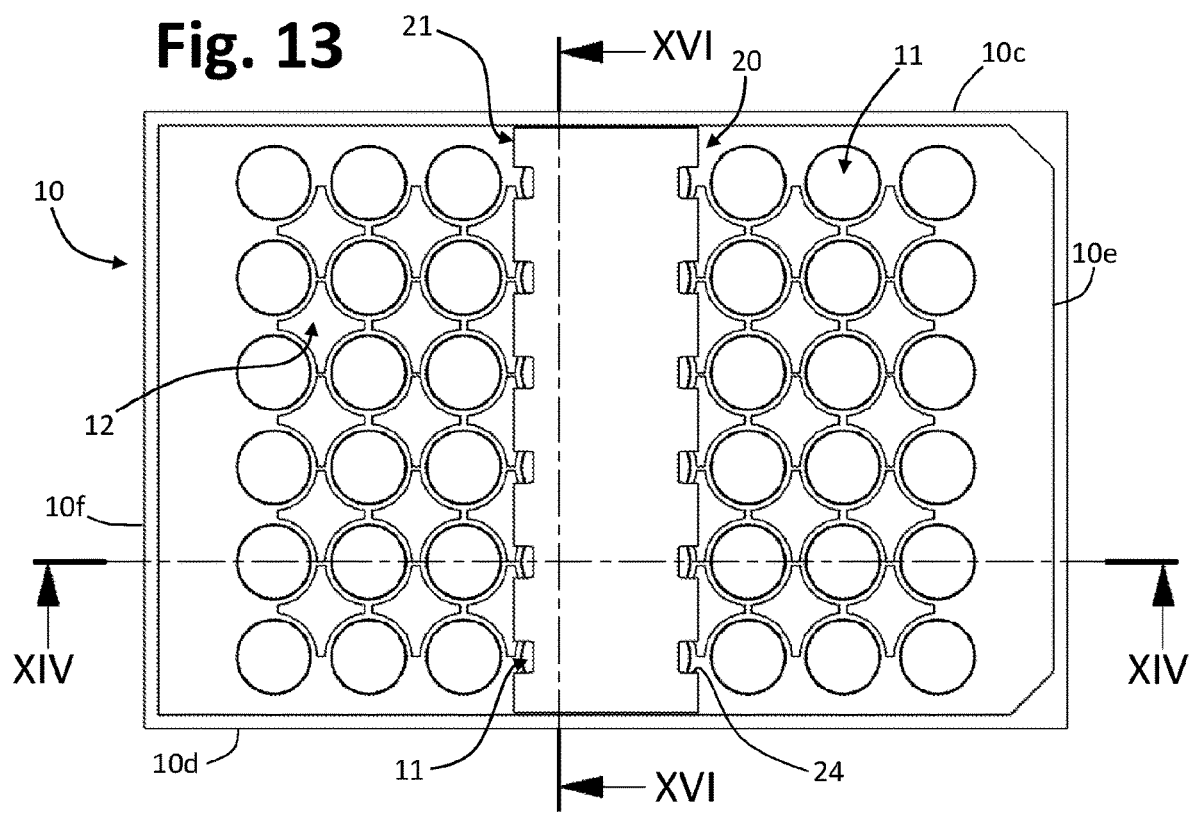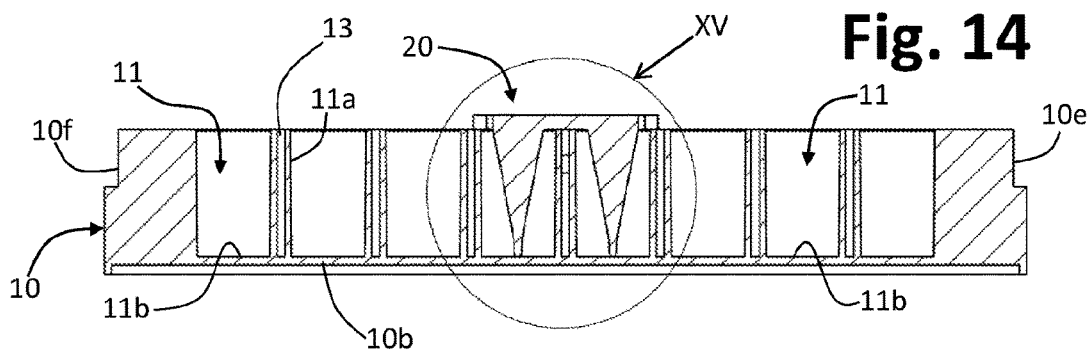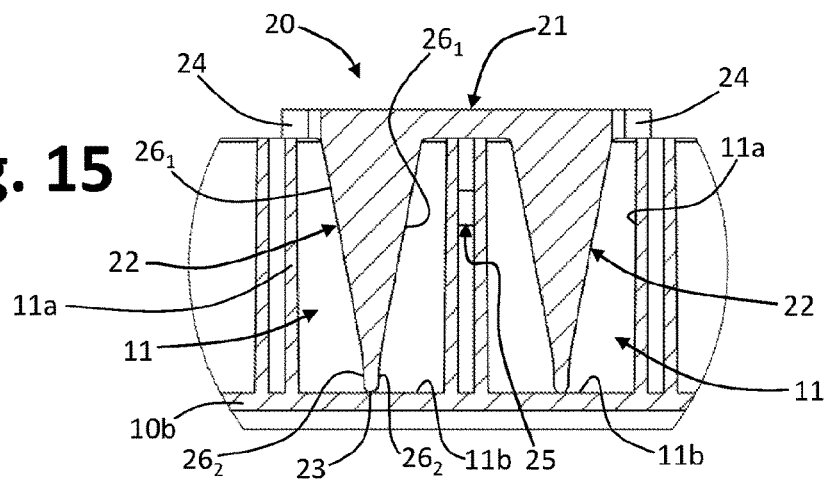

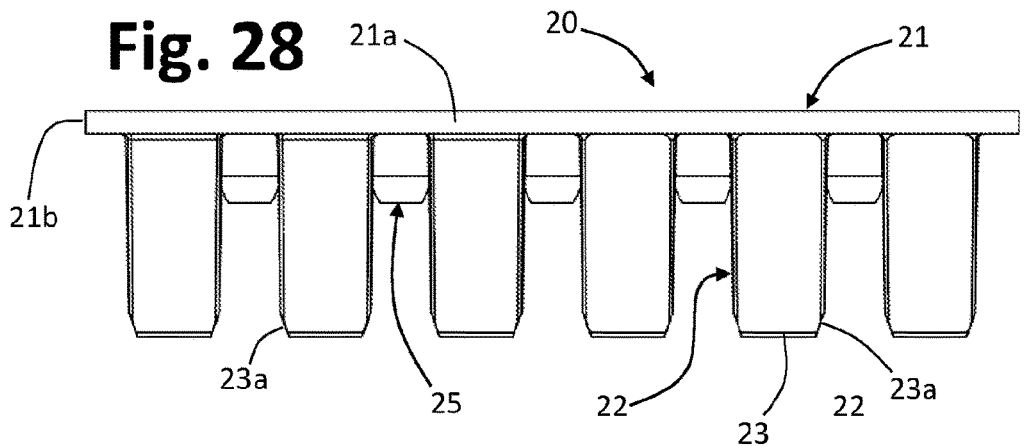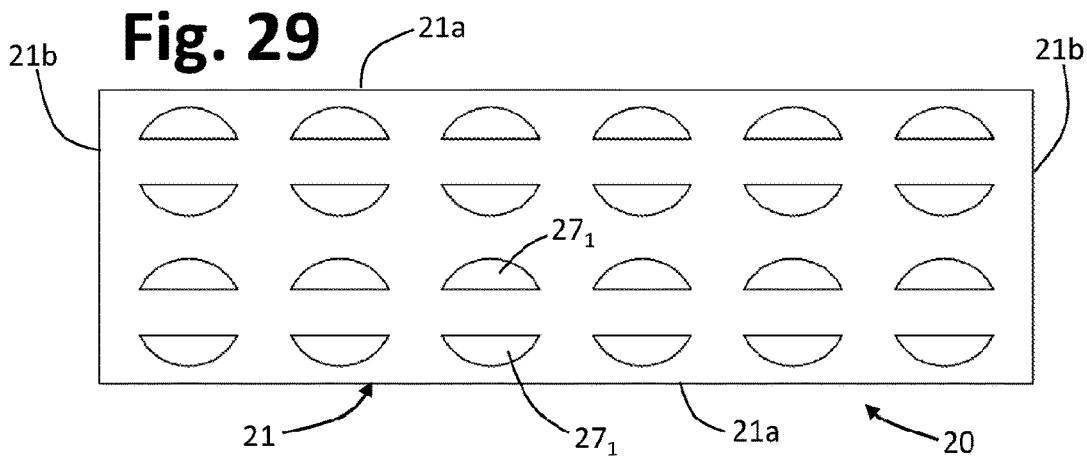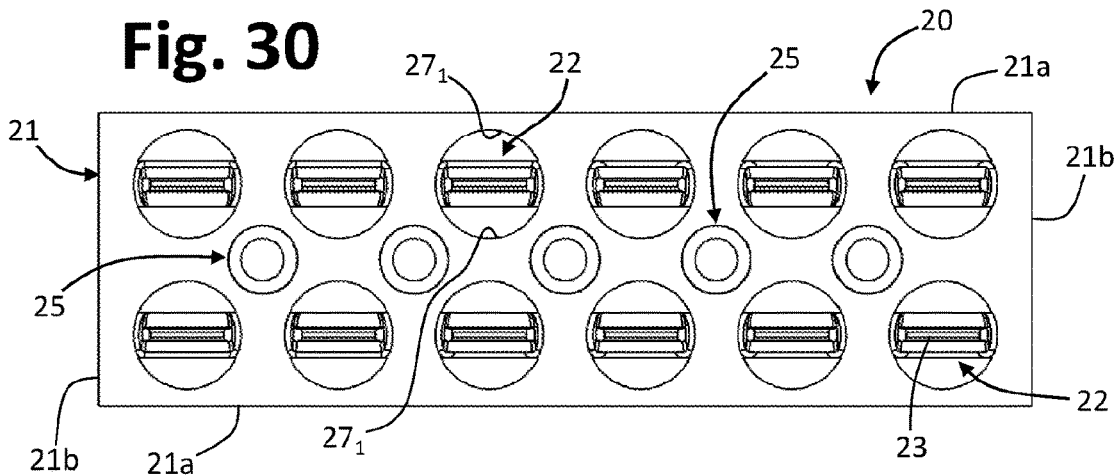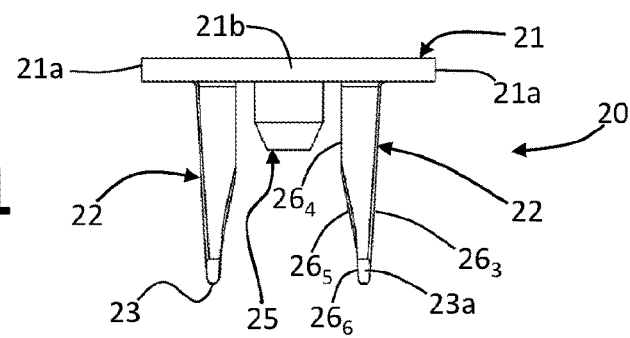

DEVICE FOR MULTI-WELL CELL-CULTURE PLATES, AND CORRESPONDING KIT

This application is the U.S. national phase of International Application No. PCT/IB2018/054911 filed Jul. 2, 2018 which designated the U.S. and claims priority to Italian Patent Application No. 102017000075491 filed Jul. 5, 2017, the entire contents of each of which are hereby incorporated by reference.

FIELD OF THE INVENTION

The present invention relates to cell cultures and to biological tissues in general, and has been developed with particular reference to devices for creating cell-exclusion zones in multi-well cell-culture plates and to kits devised for defining a plurality of zones that are to contain cells and a plurality of corresponding sub-zones free from cells. In preferred applications, the devices and kits that use the devices according to the invention are used for conducting analyses designed to determine the activity of cell features, such as cell motility, migration, or proliferation.

PRIOR ART

Biological phenomena, such as cell proliferation and migration, constitute important aspects in various pathological and physiological processes, such as wound healing, angiogenesis, embryogenesis, carcinogenic metastasis, and immune response. Wound healing, for example, is basically a biological process via which tissues of the human or animal body repair themselves after a trauma (for example, a trauma of the skin), where closing of the wound occurs thanks to the migration, which can be defined as the movement of individual cells, and/or cell sheets, and/or cell clusters from one position to another.

For the study of the migratory capacities of cells, various methodologies have been proposed, amongst which of particular interest are those based upon the use of kits designed to determine an area free from cells within a layer of cells.

Some of these kits envisage the creation of a "scratch" or "wound" in a layer of cells contained in a corresponding confined environment, typically represented by a well of a multi-well cell-culture plate. For this purpose, the cells of interest are sown in the wells of the multi-well plate, usually after introduction of a suitable culture medium, and left in the incubator in order to diffuse and form a respective layer of cells (monolayer or multilayer according to the cases) on the bottom of each well. In each layer of cells a corresponding scratch is then defined, using a mechanical implement (such as the tip of a pipette, the needle of a syringe, a blade), or possibly an electric current or electromagnetic radiation (for example, a laser beam). In this way, in the layer of cells an area free from cells is defined. The cells are then free to migrate and/or proliferate in the aforesaid free area, and, by capturing images of the layer at regular intervals, it is possible to analyse data on movement and/or proliferation of the cells during closing of the scratch.

The above kits, albeit designed to enable monitoring of the cell response, frequently entail damage to part of the cells, also with the possible release from the damaged cells of agents that may jeopardise the results of the analyses. In addition to this, the scratches made in the layers of cells of the various culture wells are in general not homogeneous; i.e., they differ from one another in terms of shape, size, and position within the various wells, and this entails, for example, the impossibility of guaranteeing equivalent conditions between control groups and experimental treatment groups.

Other kits are based upon the use of devices, also known as inserts, that each have one or more respective exclusion elements, which are to be inserted in corresponding wells of a multi-well cell-culture plate. In these inserts the bottom or distal end surface of each exclusion element is to be set in contact with the bottom of the corresponding well, prior to introduction of the cells into the latter. In this way, it is possible to exclude attachment and growth of the cells in a specific area, generally at the centre of the bottom of the well.

After the cells introduced have diffused and have covered the entire surface available of the bottom of the well (i.e., the area of the bottom that surrounds the area in contact with the distal end surface of the corresponding exclusion element), the device is removed so that an area free from cells is defined in the layer of cells. Also in this case, after removal of the device, the cells are free to migrate and/or proliferate in the free area in each well.

These kits present the advantage of enabling simulation of regular wounds, i.e., wounds that have a definite shape, and definite dimensions and positions, providing in each well a precise area of demarcation that facilitates measurement of the effective cell migration and/or proliferation. Advantageously, moreover, these devices prevent damage to the cells that are typical, instead, of scratch systems.

Known devices that can be inserted into and extracted from the multi-well plates are frequently difficult to handle and position and frequently require extractor tools.

To facilitate extraction without tools, in some cases the devices each comprise a single exclusion element that must be set in a position corresponding to a respective well. During coupling of each device with the corresponding well, the operator responsible for carrying out the analysis should make sure that the various devices are positioned correctly to enable uniformity of analysis. These circumstances imply significant times for preparation of the tests, even in the case of use of specific positioning tools on which the individual devices are to be previously arranged.

In other cases, known devices envisage a number of exclusion elements that are to be inserted in respective wells, which, however, are in general of a limited number (typically from four to eight exclusion elements), and also in these cases specific tools must be normally used for positioning and subsequent removal of the device relative to the culture plate. In addition to the difficulty of handling of the ensemble made up of the tool and the devices, also these systems imply significant times for preparation of the test, for example in the case of culture plates that have 48 or 96 wells.

In other cases still, the devices are not suitable for being used with culture plates of a standard type, but must instead be applied to plates of a specifically dedicated type.

In practice, the devices currently commercially available involve various steps for setting up an experiment and significant lengths times for manual activity, as well as frequently the use of specific handling tools.

AIM AND SUMMARY OF THE INVENTION

The present invention is basically aimed to provide a device for creating cell-exclusion zones in a multi-well cell-culture plate that is simple and economically advantageous to produce and easy to handle and/or position, and does not necessarily require specific tools for its insertion into and/or removal from a multi-well cell-culture plate. Another aim of the present invention is to provide a device of the type referred to that can be produced easily in various versions that include even a large number of exclusion portions, for example between 12 and 96 exclusion portions for use in corresponding multi-well plates. Yet a further aim of the invention is to provide a device of the type referred to that is suitable for use in combination with culture plates of a standardised, i.e., commercial, type. Another aim of the invention is to provide a device of the type referred to that can be easily fixed to, and/or positioned in, and/or removed from, culture plates.

One or more of the aforesaid aims is achieved according to the present invention by a device for creating cell-exclusion zones in a multi-well cell-culture plate having the characteristics referred to in the annexed claims. Likewise forming the subject of the invention is a kit that uses such a device according to the invention and a method for using such a kit. Preferred characteristics of the device, of the kit, and of the method for use thereof are specified in the dependent claims. The claims form an integral part of the technical teaching provided herein in relation to the invention.

BRIEF DESCRIPTION OF THE DRAWINGS

Further aims, characteristics, and advantages of the invention will emerge clearly from the ensuing description, with reference to the annexed drawings, which are provided purely by way of non-limiting example and in which:

FIG. 13 is a schematic top plan view of the kit of FIG. 1;

FIG. 14 is a schematic cross-sectional view according to the line XIV-XIV of FIG. 13;

FIG. 15 illustrates the detail XV of FIG. 14 at a larger scale;

FIGS. 28, 29, 30, and 31 are schematic views, in side elevation, from above, from beneath, and in front elevation, respectively, of the device of FIGS. 26-27;

DESCRIPTION OF PREFERRED EMBODIMENTS OF THE INVENTION

Reference to "an embodiment", "one embodiment", "various embodiments", and the like, in the framework of the present description, is intended to indicate that at least one particular configuration, structure, or characteristic described in relation to the embodiment is comprised in at least one embodiment. Hence, phrases such as "in an embodiment", "in one embodiment", "in various embodiments", and the like that may be present in various points of this description do not necessarily refer to one and the same embodiment, but may instead refer to different embodiments. Moreover, particular conformations, structures, or characteristics defined in the framework of this description may be combined in any adequate way in one or more embodiments, even different from the ones represented. The reference numbers and spatial references (such as "upper", "lower", "top", "bottom", "front", "back", "vertical", etc.) used herein, in particular with reference to the examples in the figures, are provided merely for convenience and hence do not define the sphere of protection or the scope of the embodiments. In the figures, the same reference numbers are used to designate elements that are similar or technically equivalent to one another.

Figure 1:
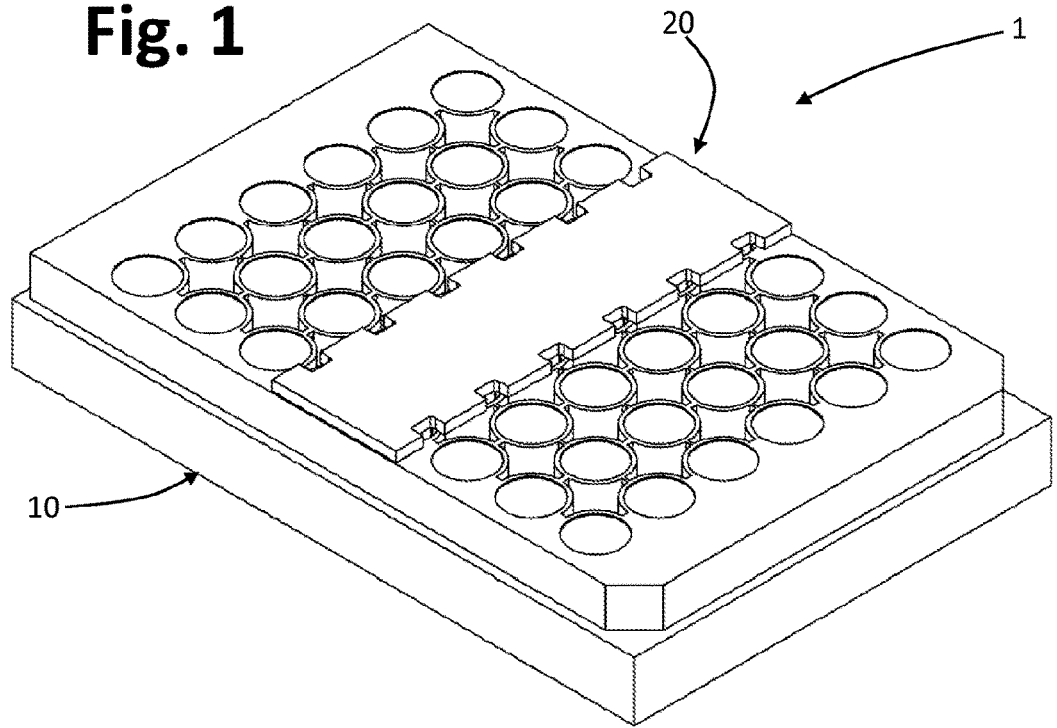
FIG. 1 is a schematic perspective view of a kit suitable for conducting analyses on the activity of cell features, which uses at least one device for creating cell-exclusion zones, according to possible embodiments of the invention.
Figure 2:
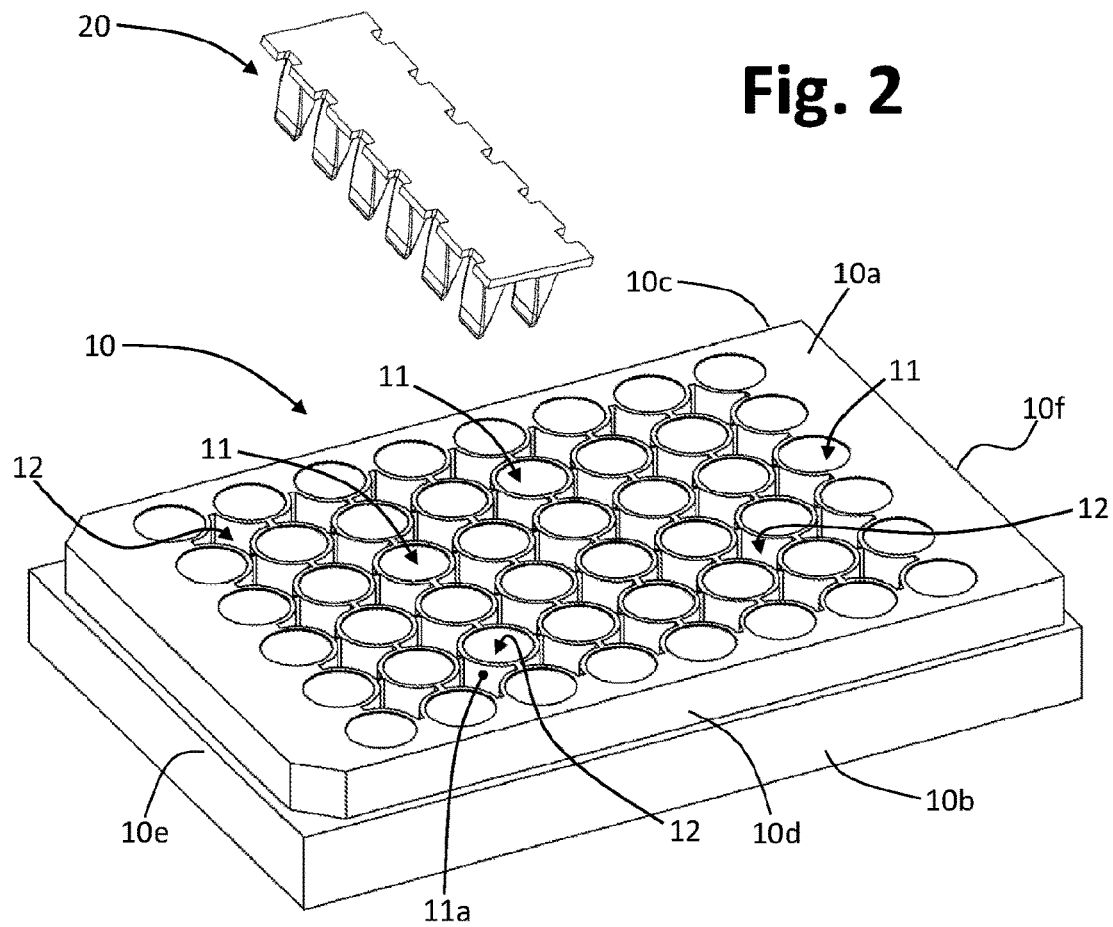
FIG. 2 is an exploded schematic view of the kit of FIG. 1.

With initial reference to FIGS. 1 and 2, designated as a whole by 1 is a kit suitable for conducting examinations or tests, in particular for determining the activity of tissues or cell features, such as cell motility, migration, or proliferation. In the sequel of the present description it is assumed that, for this purpose, the kit 1 is used for creating cell-exclusion zones, aimed at studying cell migration or proliferation.

The kit 1 comprises a multi-well culture plate, designated as a whole by 10, and a device for creating cell-exclusion zones, designated as a whole by 20. Given that the device 20 is to be partially inserted in the plate 10, it will be defined in what follows also as "insert".

In various preferred embodiments—such as the one exemplified—the multi-well plate 10 is a plate of a standardised type, i.e., of a type commonly available on the market. In the case illustrated, the plate has 48 wells, but the invention may in any case be applied also to culture plates that have a different number of wells, for example 6, 12, 24, 48, or 96 wells. The plate 10 preferentially has a body made of a biocompatible stiff material, preferably a plastic material, such as polystyrene. The body of the plate 10 may be advantageously made of a single piece obtained via moulding.

Figure 3:
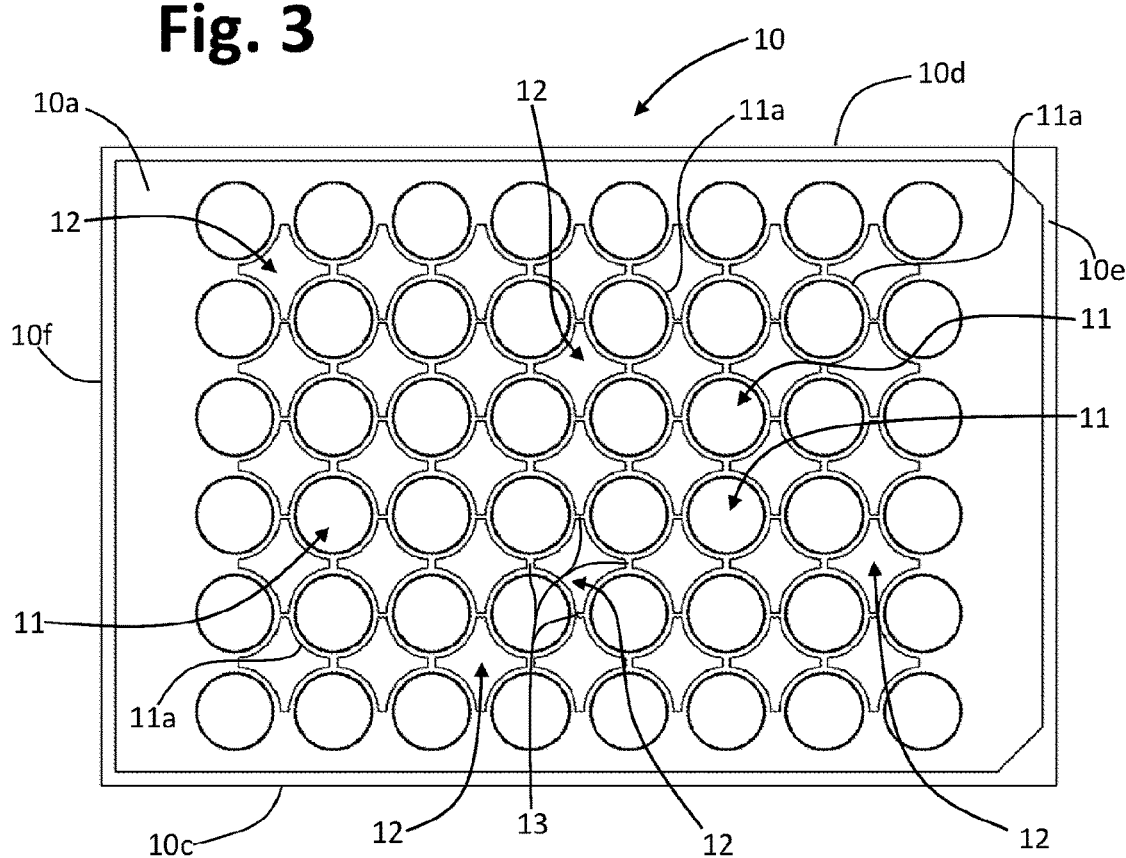
FIG. 3 is a top plan view of a multi-well cell-culture plate forming part of the kit of FIG. 1.
Figure 4:
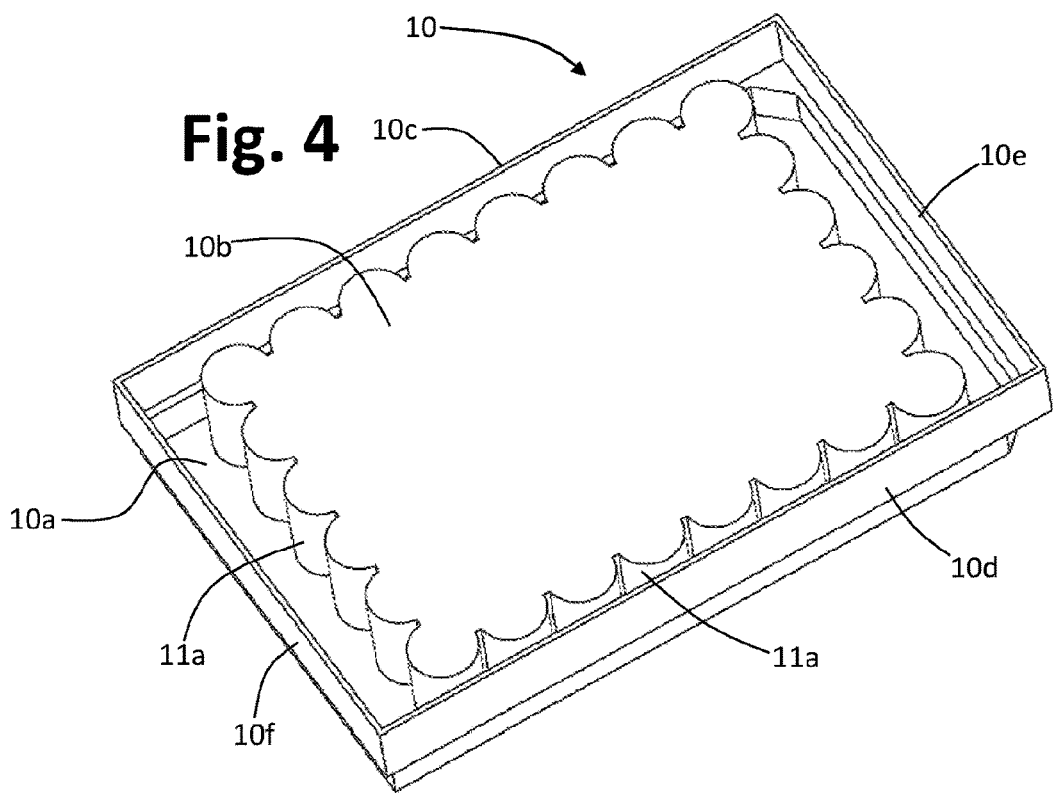
FIG. 4 is a schematic perspective view of the back of a plate of the type illustrated in FIG. 3.
Figure 5:
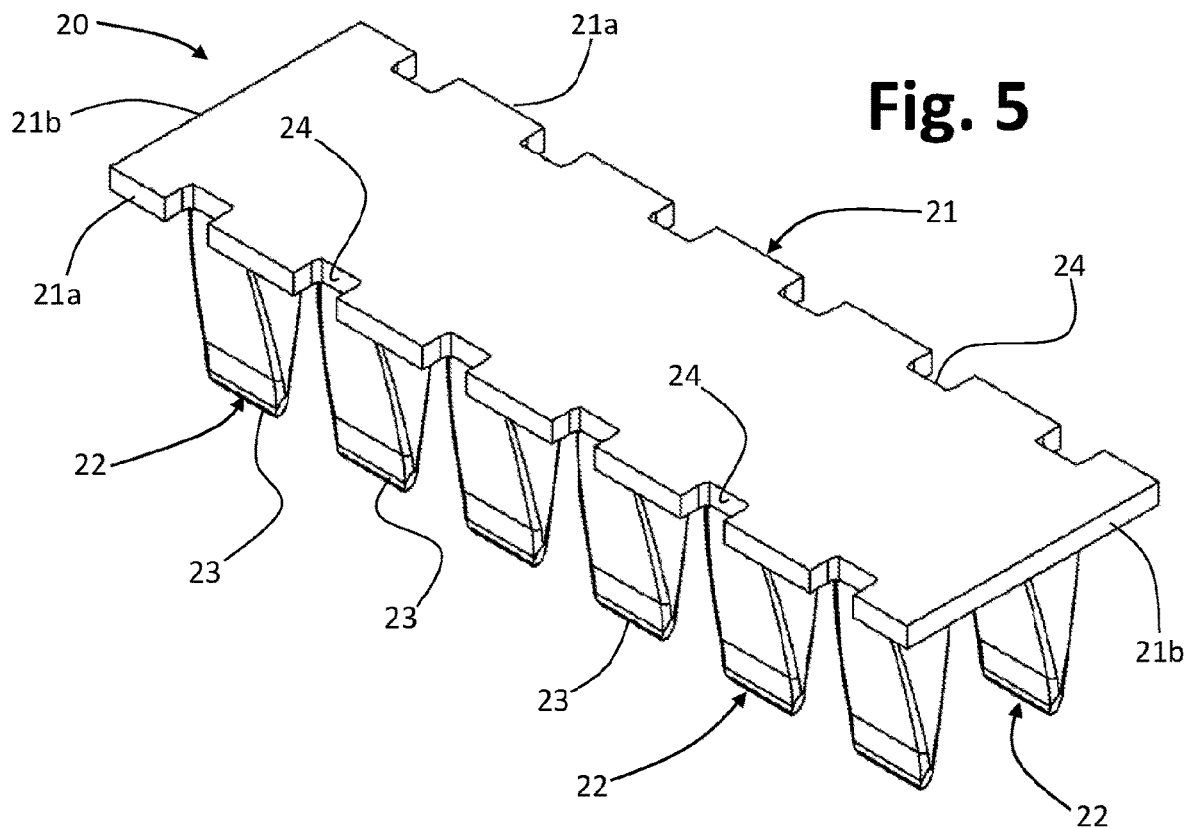
FIGS. 5 and 6 are schematic perspective views from different angles of a device of the kit of FIG. 1.
Figure 6:
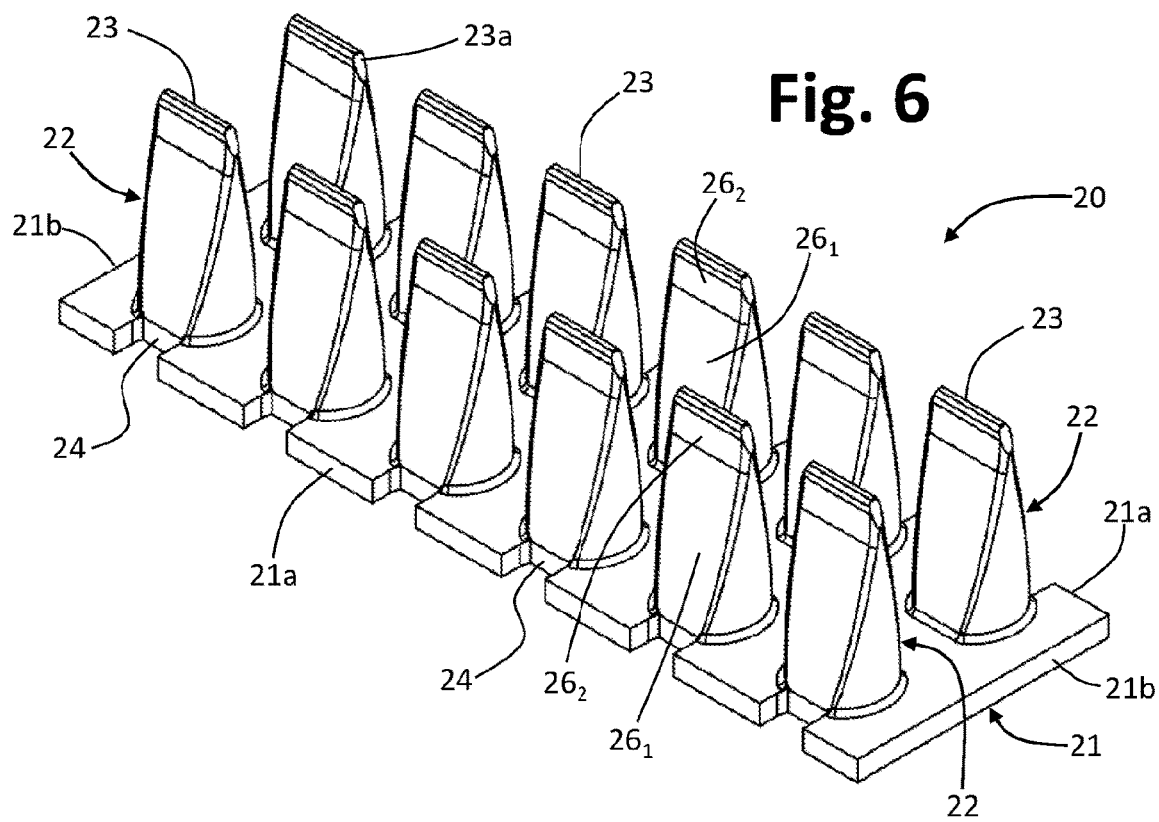
Figure 7:
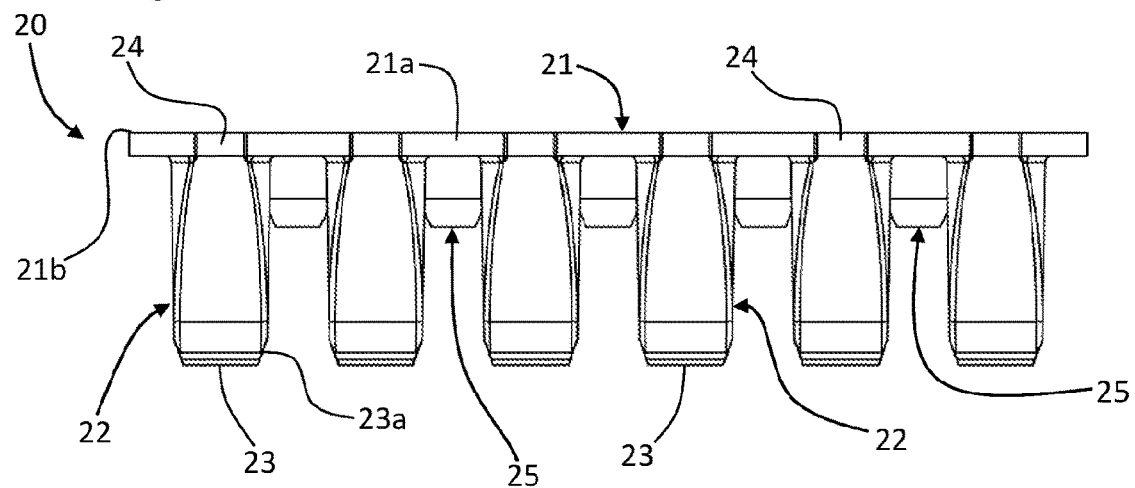
FIGS. 7, 8, 9, and 10 are schematic views, in side elevation, from above, from beneath, and in front elevation, respectively, of the device of FIGS. 5-6.
Figure 8:
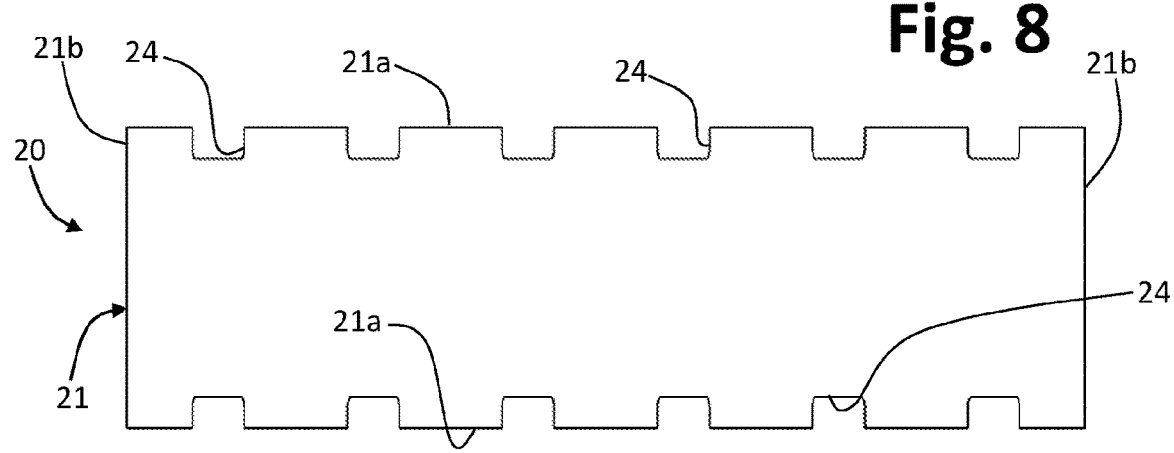

With reference also to FIGS. 3 and 4, in the example, the body of the plate 10 has a top face 10a, preferably plane, where a plurality of wells 11 open, as well as a lower wall—designated by 10b in FIG. 4—which defines a bottom of the wells 11, designated by 11b, for example in FIGS. 14-15. The body of the plate 10 is basically shaped so as to define a peripheral structure that surrounds or circumscribes a region within which the wells 11 are located. For this purpose, in the example represented, the body of the plate 10 has a generally quadrangular outer profile, delimited by four sides 10c, 10d, 10e, and 10f, here arranged substantially in the form of a rectangle. The sides 10c-10f are preferentially provided on the outside with an intermediate step-like formation, not designated by any reference number but clearly visible, for example, in FIGS. 1 and 2, and the lower wall 10b is at least slightly recessed with respect to the sides themselves (see FIGS. 14 and 16). In this way, thanks to the presence of the aforesaid step and of the recessed bottom, a plurality of plates 10 can be stacked on top of one another, for example for the purposes of storage. The wells 11 are preferentially arranged in an array configuration, i.e., in a plurality of parallel rows or columns, and are configured for defining a hollow volume, which is preferably but not necessarily cylindrical.

The wells 11 are delimited peripherally by respective walls, preferably cylindrical, designated by 11a. As also visible in FIGS. 4, 14, and 16, the lower wall 10b of the body of the plate 10 defines the bottom 11b of each well of the array. Alternatively, each well 11 may be provided with a respective bottom wall.

In various embodiments, the wells 11 that are located at the sides 10c-10f (i.e., the wells closest to said sides) are provided with respective cylindrical walls 11a, separate from the aforesaid sides 10c-10d (see FIG. 4) or else joined to said sides and/or to one another via thin vertical plane walls, substantially of the type designated hereinafter by 13.

In other embodiments, the sides 10c-10f have, instead, a full structure (as exemplified, for instance, in FIGS. 12, 14, 16, and 17), with their part facing the centre of the plate 10 that is shaped so as to define vertical recesses, which have a substantially semicircular cross section. In these embodiments, the aforesaid semicircular recesses define, together with respective semicircular vertical walls, the peripheral surface of the wells 11 closest to the sides 10c-10f. Once again for the case of sides 10c-10f with full structure, the four wells 11 at the corners of the array of wells have a peripheral surface that is, instead, defined by vertical recesses that develop along an arc through approximately 270°, at the intersection between two orthogonal sides, together with vertical walls that have an arched cross section and develop through approximately 90°.

As may be noted in particular in FIG. 3, the arrangement of the wells, i.e., of the respective walls 11a, in an array determines the presence of gaps 12 in an area that is central with respect to four wells 11. In the example, these gaps 12 have a cross section approximately shaped like a rhombus with arched sides, i.e., substantially shaped like an astroid. Preferentially, the arched walls 11a of the various wells are not tangential to one another, but are at least slightly set at a distance apart and joined by means of small substantially plane vertical walls or with some other appropriate shape, some of which are designated by 13 in FIG. 3. In the example, the aforesaid vertical walls 13 define the four vertices of the gaps 12. It should be noted that, in other embodiments, the configuration of the plate could differ slightly from the one exemplified: for example, the joining walls 13 between the various wells 11 could be absent.

The configuration referred to for the culture plate 10 is basically of the type commonly available on the market, apart from the number of wells 11, which, as has been said, may be variable. In general, the inner diameter of the wells 11 may be between 5.0 and 45.0 mm, their height or depth may be between 5.0 and 20.0 mm, and the distance between the central axes of two contiguous wells may be between 5.0 and 45.0 mm. For instance, in the case of a plate with 10 to 96 wells, the diameter may be approximately 6-7 mm, the height approximately 11 mm, and the centre-to-centre distance approximately 9 mm, and in the case of a plate with 6 wells, the diameter may be approximately 35 mm, the height approximately 18 mm, and the centre-to-centre distance approximately 38 mm.

With reference now to FIGS. 5-10, the structure of the device or insert 20 comprises a baseplate, designated by 21, preferably having a perimeter that is substantially quadrangular, very preferably substantially rectangular. Projecting from a major face of the baseplate 21—hereinafter defined conventionally also as "lower face"—are a plurality of exclusion reliefs 22, which are preferably arranged according to at least an orderly series, such as to enable insertion thereof in respective wells of a corresponding culture plate 10.

In the non-limiting example illustrated, the insert 20 comprises two rows or parallel series of six reliefs 22, but in other embodiments (as described hereinafter) the insert may comprise more than two parallel rows of reliefs 22, or possibly even a single row of reliefs, and the number of reliefs of each row may be other than six. In general, the length of the baseplate 21 corresponds at least approximately to the distance between two opposite sides 10c-10d or 10e-10f of the culture plate 10, it possibly having a shorter length, for example in the case where the number of reliefs 22 corresponds to a fraction or a submultiple of the total number of wells 11 in a row or column of the plate 10 (for example, three reliefs 22 in the case of a plate with rows of six wells 11).

Each exclusion relief 22 has a lower or distal end 23, which is configured for contact with the bottom 11b of a respective well 11 of the plate 10 (see, for example, FIG. 15). For this purpose, of course, the dimensions of the reliefs 22, in terms of length, width, and centre-to-centre distance, are defined according to those of the wells 11 of the plate 10. For instance, visible in FIGS. 13-18 is the condition that follows on coupling of the insert 20 on the culture plate 10, with the exclusion reliefs 22 inserted in corresponding wells 11 and with the distal ends 23 of the reliefs 22 in contact with the bottom 11b of the wells themselves. The reliefs 22, or in any case their distal ends 23, may be arranged according to one and the same orientation, for the purposes of homogeneity or practicality of analysis. Preferentially, the distal end surface of the reliefs 22 is substantially flat, in order to guarantee an elastic adhesion that is as precise as possible to the bottom 11b of the corresponding well 11. Once again preferably, the distal ends 23 of the reliefs, namely, the corresponding cross sections in a plane parallel to the bottom 11b, extend in a substantially rectilinear way; i.e., they extend in the direction of a respective axis parallel to the bottom 11b.

According to the invention, the baseplate 21 and the plurality of exclusion reliefs 22 of the insert 20 are made at least in part of elastic or flexible material, in such a way that at least the baseplate 21 is elastically deformable or can bend at least in part, at least during removal thereof from the culture plate 10. In preferential embodiments, the baseplate 1 and the reliefs 22 are defined by one and the same body made of the aforesaid elastic or flexible material.

In various embodiments, the portions of the baseplate 21 of the device 20 comprised in the intermediate or connection areas between the exclusion reliefs 22, in particular the areas comprised between the proximal or upper ends of the reliefs 22, are at least in part flexible or deformable. At least the baseplate 21 may be reinforced via fibres or inserts that are at least in part flexible, in any case designed to enable at least a partial bending of the baseplate 21 and/or of the aforesaid intermediate or connection areas between the exclusion reliefs 22. This albeit minimal bending enables raising in a sequential way of the exclusion reliefs 22 and of the corresponding fixing means with respect to the plate 10, thus reducing the effort required for extraction even in the case of inserts of large dimensions, which should otherwise be raised and extracted via purposely provided tools, for example on account of the high force or friction caused by the simultaneous disengagement of the means for coupling of the insert 20 to the plate 10.

Use of the aforesaid flexible elastic material moreover makes it possible to define, for the various exclusion reliefs 22, distal ends 23 that are designed to adhere to or rest elastically on the smooth and flat bottom surface 11b of the wells 11 (which is cleaned and dried before an experiment is carried out), for the purposes of creation of the exclusion zones for cell growth in a culture plate 10.

The fact that the exclusion reliefs 22 are elastically deformable, i.e., compressible, moreover enables use of inserts according to the invention even in sensorised multi-well plates, i.e., in plates of the type where, at the bottom of each well, electric sensors are provided, used for treatment and/or monitoring of the sample of cells or tissue. As will be seen, these plates may have a standard structure of the type described above, and the sensors present on the bottom 11b of the wells usually comprise electrodes of a comb-fingered type. In various preferred embodiments, the reliefs 22 are as a whole deformable or compressible, and this prevents risks of damage to the aforesaid sensors or electrodes in the course of coupling of the insert 20 to the sensorised plate, as may, instead, happen in the case of exclusion elements having a substantially stiff structure, provided with a compliant coating only at their distal ends.

In various preferential embodiments, the exclusion reliefs 22 are at least in part, preferably throughout their length, made of a material that is at least in part deformable, or compressible, or compliant. This enables better compensation of possible variations of the length of the wells 11 and/or of the exclusion reliefs 22, which are typically present as a result of production tolerances following upon moulding of the thermoplastic or elastomeric materials. In this way, the aforesaid dimensional variations are not concentrated just in the area in contact with the bottom of a well 11, hence preventing in the aforesaid end area significant axial deformations or squeezing that otherwise would lead to major lateral deformations and consequent considerable variations in the impression in the cell-exclusion zone, thus altering the measurements.

The preferential solution according to the invention, with plate 21 and reliefs 22 in a single body, moreover makes it possible to provide in a very simple and economically advantageous way inserts 20, i.e., to produce a wide range of inserts that have a variable number of reliefs 22, via simple moulding operations, in particular injection-moulding operations.

The preferred materials used for formation of the insert preferably comprise biocompatible elastic or flexible materials of synthetic origin, such as elastic polymers or elastomers, for example silicone, but not excluded from the scope of the invention is the use of a natural material, such as rubber (it should be noted that the term "material" used herein is intended to designate either a single material, for example a silicone, or different mixtures or combinations of materials). For instance, in various embodiments, co-moulding or overmoulding of a number of materials may be envisaged, for example, with an insert made of a relatively stiffer or non-elastic material, overmoulded on which is at least one more elastic or flexible material, such as an elastomer, or else with an insert made of a number of elastic or flexible materials, for example two elastomers with different hardness. In general, the preferred elastic materials are those that have a hardness comprised between 10 and 90 Shore A, preferably between 30 and 50 Shore A.

According to an inventive aspect, the insert 20 may comprise constraint means, for coupling and/or positioning with respect to the culture plate 10, and/or the culture plate 10 may comprise constraint means for coupling and/or positioning thereof with respect to the insert 20. These constraint means, which perform functions of coupling and/or positioning of the insert 20 with respect to the plate 10, may for example be in the form of elements in relief, or seats, or hooks, or means for fixing via coupling or interference fit. In preferred embodiments, both the insert 20 and the plate 10 comprise respective constraint means, which are preferably functionally complementary to one another.

In the present description and in the attached claims, the term "coupling" is intended to indicate the function of (albeit temporary) fixing of the insert 20 to the plate 10, which is preferentially obtained via an anti-slip coupling by interference, substantially in a vertical direction, whereas the term "positioning" is intended, instead, to indicate the function of centring of the exclusion reliefs 22 within the wells 11, preventing the former from possibly accidentally displacing with respect to the latter in a lateral direction.

In advantageous embodiments, both the function of coupling and the function of centring are obtained by the same constraint means.

For instance, in preferred embodiments, projecting from the bottom face of the baseplate 21 of the insert 20 is a plurality of constraint reliefs, designated by 25, which are configured for coupling in corresponding seats of a multi-well cell-culture plate 10. In this way, a precise coupling and mutual positioning between the plate 10 and the insert 20 is guaranteed, where in particular the constraint reliefs 25 "self-centre" in the respective seats thanks to their elasticity, consequently centring the exclusion reliefs 22 in the wells 11.

Figure 9:
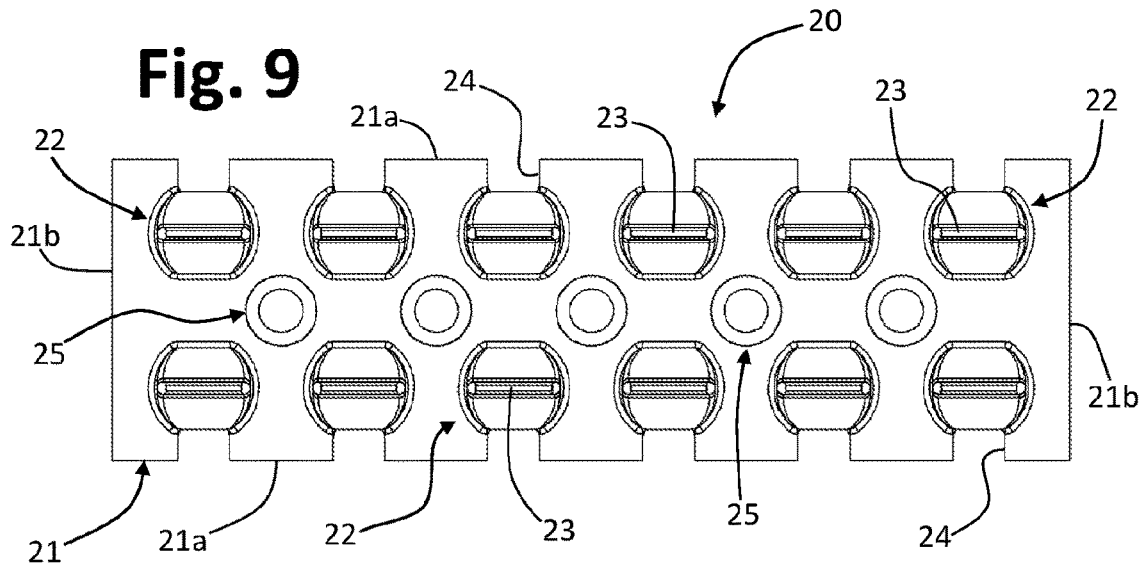
Figure 10:
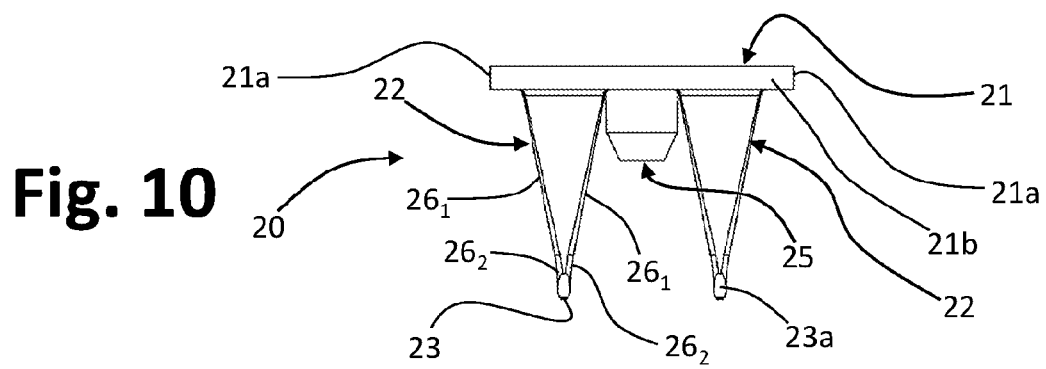
Figure 11:
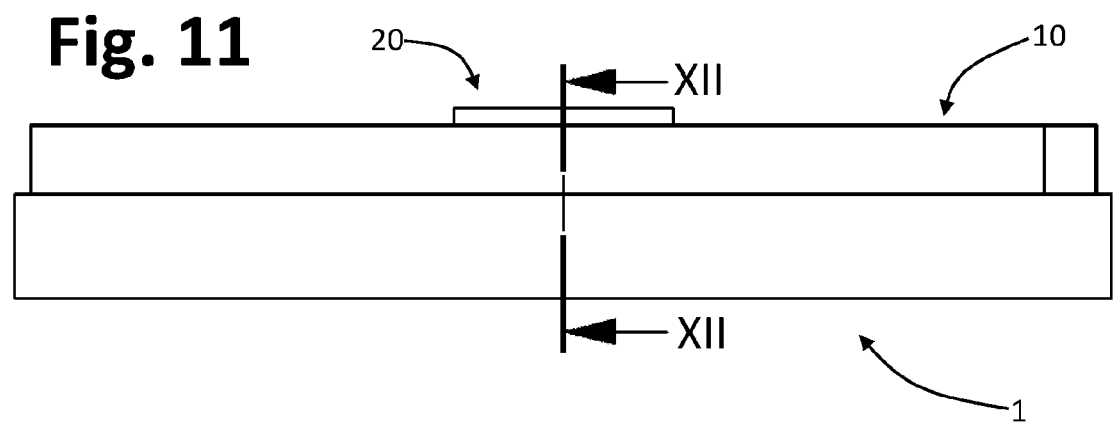
FIG. 11 is a schematic side view of the kit of FIG. 1.
Figure 12:
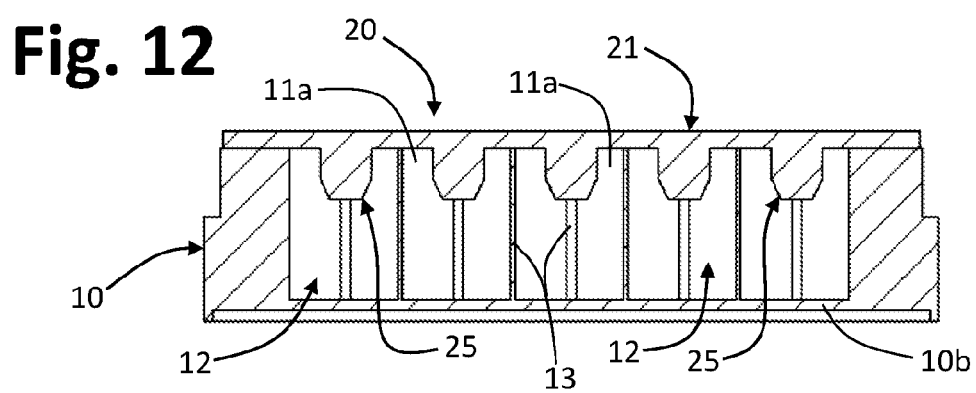
FIG. 12 is a schematic cross-sectional view according to the line XII-XII of FIG. 11.
Figure 19:
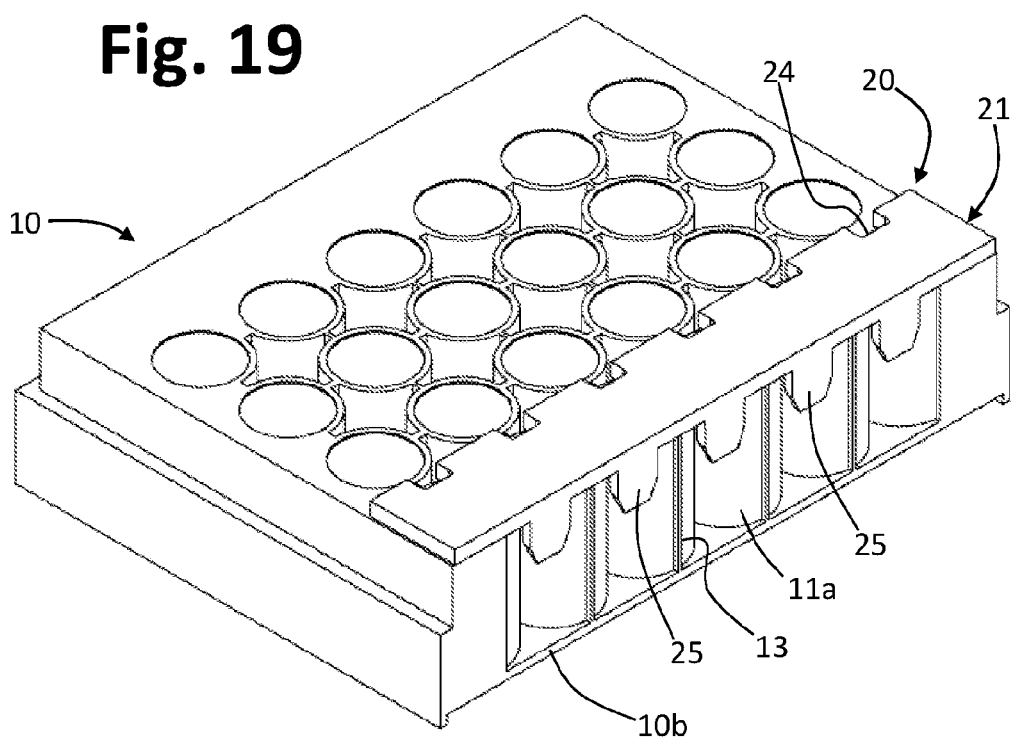
Figure 20:
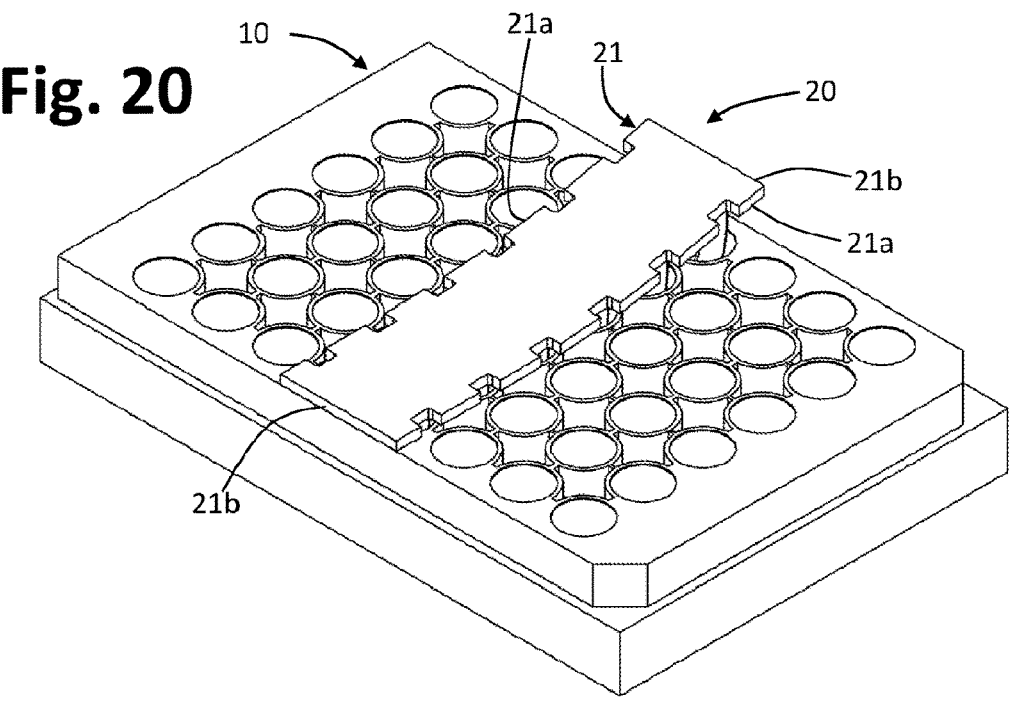
FIG. 20 is a schematic perspective view of the kit of FIG. 1, in a step of removal of the device from (or insertion of the device into) the corresponding multi-well plate.
Figure 21:
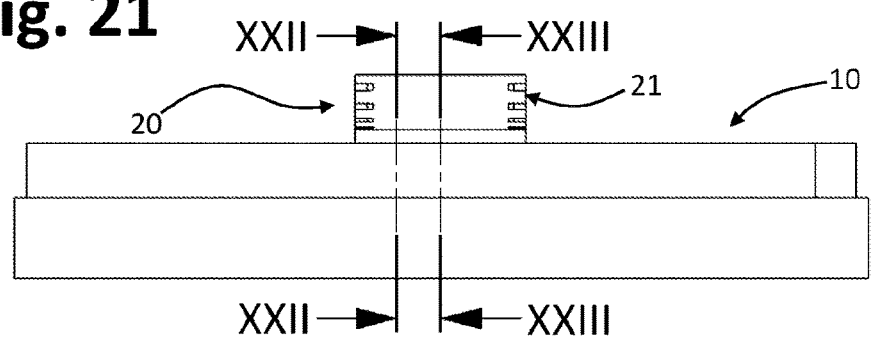
FIG. 21 is a schematic side view of the kit of FIG. 20.
Figure 22:
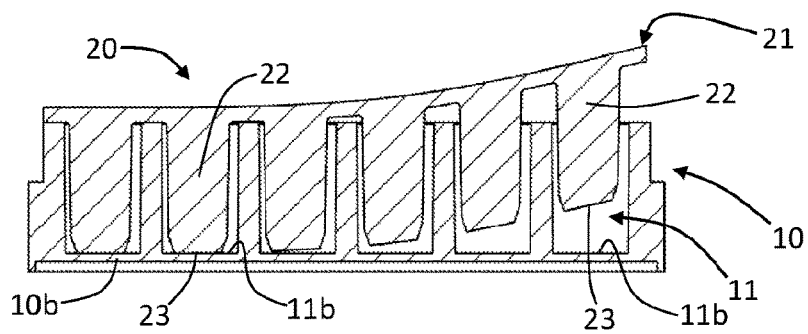
FIGS. 22 and 23 are schematic cross-sectional views according to the lines XXII-XXII and XXIII-XXIII of FIG. 21, respectively.
Figure 23:
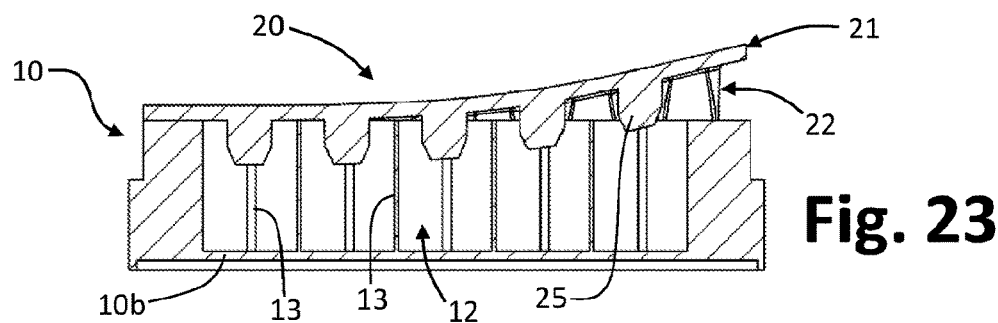

In various embodiments, when the insert 20 envisages a number of parallel series of exclusion reliefs 22, the constraint reliefs 25 are each preferably defined in a substantially central position relative to four contiguous exclusion reliefs 22 (see, for example, FIG. 9). In this way, with reference to the example illustrated in the figures, the constraint reliefs 25 are able to engage in the gaps 12 of the culture plate 10, with the aforesaid gaps 12 that are then exploited as constraint seats, i.e., coupling and/or positioning seats, for the insert 20. The condition of coupling of the reliefs 25 within the gaps 12 may, for instance, be seen in FIGS. 12 and 19.

In various preferred embodiments, the constraint reliefs 25 are defined by the same elastic or flexible material that forms the baseplate 21 and the exclusion reliefs 22; i.e., they are preferably made in a single body therewith. In this way, the constraint reliefs 25 can be coupled/uncoupled in an elastic way to/from the plate 10, especially to/from its gaps 12, in particular via elastic interference and/or elastic deformation of the constraint reliefs 25, and production of the insert 20 is further simplified (i.e., it does not require assemblage thereto of additional components). The constraint reliefs 25 may have any shape suitable for the purpose: in the case exemplified, the reliefs have a substantially cylindrical shape, with the respective distal end generally flared or frustoconical (see, for example, FIGS. 7 and 12), but they could also have, for example, a shape that is as a whole frustoconical, or a shape with square or rhomboidal section, or an astroid-shaped section, or may have any other shape that is at least in part complementary to the shape of the gaps 12 of the culture plate 10, or a shape that enables insertion with elastic interference, also via deformation and variation of the shape of the constraint reliefs 25 so that they can elastically adapt to and be inserted in the gaps 12.

Preferentially, the exclusion reliefs 22 are massive, i.e., full (possibly being at least in part hollow or themselves comprising internal inserts). In addition to simplifying production of the insert 20, this solution makes it possible to bestow a certain structural stiffness upon the reliefs 22, without jeopardizing their capacity of elastic deformation. For the same reason, also the constraint reliefs 25 may be massive.

In various preferred embodiments, the exclusion reliefs 22 have a main cross section with a shape that tapers towards the distal end 23; for example, they are substantially wedge-shaped (i.e., shaped like a prism with triangular cross section) or frusto-pyramidal, possibly provided with stiffening edges or ribbings, or more in general with at least two substantially plane opposite walls, preferably inclined with respect to one another at least in part in opposite directions. The shape that at least in part tapers makes it possible to have a distal end 23 of the reliefs 22 sufficiently small to define the exclusion zones within the wells 11, in any case guaranteeing the aforesaid structural stiffness of the reliefs 22 as a whole. Consequently, in various embodiments, each exclusion relief 22 has at least two opposite faces that are generally convergent, preferably starting from the baseplate 21.

The above opposite faces may present stretches of surface that are differently inclined, or else have a constant inclination. For instance, in the case of the embodiments represented in FIGS. 1-23, each of the two convergent faces of the reliefs 22 has two stretches of surface with different inclination, designated by $26_1$ and $26_2$, for example in FIGS. 6, 10, and 15. It is preferable, in order to provide cell-exclusion zones that are as precise as possible, for the convergent faces of each relief 22 to be shaped so as to extend at least approximately parallel (where "approximately parallel" is meant to comprise also minor relative inclinations) at least in a distal end portion of the relief itself. For instance, in the specific case of FIGS. 10 and 15, the stretches of surface $26_2$ are only slightly inclined with respect to one another; i.e., they almost parallel. The decreasing or tapered cross-sectional shape of the reliefs 22 likewise facilitates production via moulding of the inserts 20, facilitating extraction thereof from the corresponding production moulds.

According to various embodiments, it is also possible to provide the reliefs 22 with lateral rounded edges at their distal end 23 designed for contact with the bottom 11b of a corresponding well 11. These rounded edges, such as the ones designated by 23a in FIGS. 6, 7, and 10, may prove advantageous in the production stage, in particular to facilitate extraction and detachment of the insert 20 from the mould, after the corresponding moulding operation.

In various embodiments, the baseplate 21 has at least one edge provided with a plurality of recesses or openings; in the case of the embodiments of FIGS. 1-23, recesses—some of which are designated by 24—are provided at two opposite edges of the baseplate 21. In the example illustrated, these edges are the longer edges 21a of the baseplate 21 but, in principle, recesses or openings 24 could (also) be provided at the shorter edges 21b.

Each recess (or opening) 24 is preferentially defined at the respective edge 21a of the baseplate 21 in a position that is lateral with respect to an exclusion relief 22, which is closest to said edge 21a, and is configured, in particular in terms of dimensions and position, to enable access to a well 11 of the culture plate 10, in which the exclusion relief 22 in question is inserted, when the insert 20 is coupled to the culture plate 10. Preferentially, the recess (or opening) 24 enables at least partial insertion and/or resting of a serological pipette, such as a pipette made of glass or polymer. According to an inventive aspect, the recess or opening is delimited at least in part by an elastic material—in particular the same elastic or flexible material as that of the plate 21 and/or of the reliefs 22 and/or of the reliefs 25, such as an elastomer—which enables elastic resting, and/or sealing, and/or shape fitting of the recess or opening with respect to the pipette. This characteristic prevents, for example, the risk of breaking of brittle pipettes, such as glass pipettes, in particular in the case of anomalous accidental movements by the operator, and/or enables sealing between the pipette and the baseplate 21. This characteristic is clearly visible, for example, in FIGS. 15 and 50, where it may be noted how the presence of the recesses 24 enables at least partial insertion of a tool or instrument 8 (for example, a pipette) into the well 11 in which a respective relief 22 extends.

Figure 16:
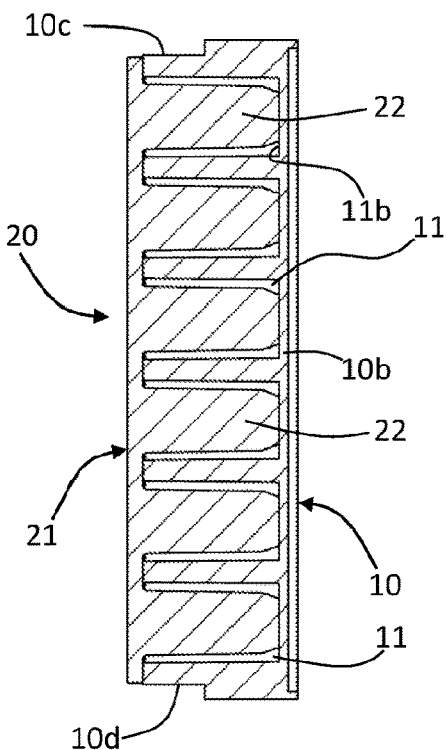
FIG. 16 is a schematic cross-sectional view according to the line XVI-XVI of FIG. 13.
Figure 17:
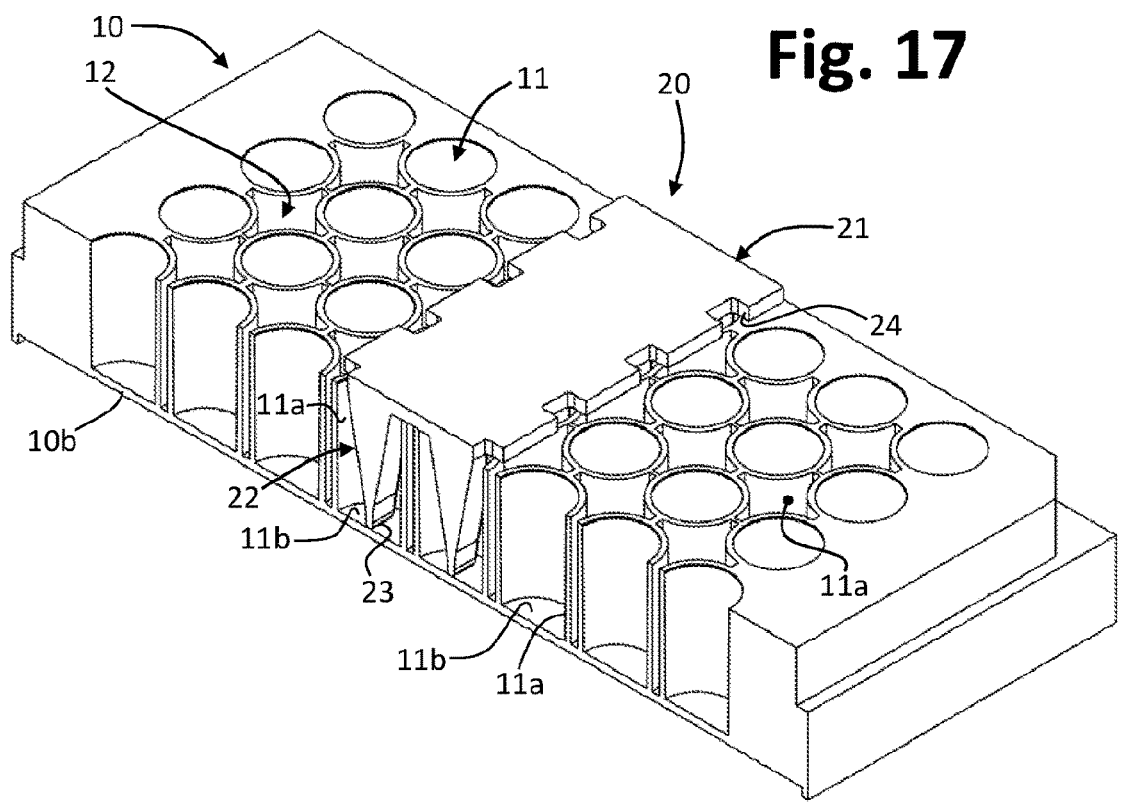
FIGS. 17, 18, and 19 are sectioned perspective views of the kit of FIG. 1.
Figure 18:
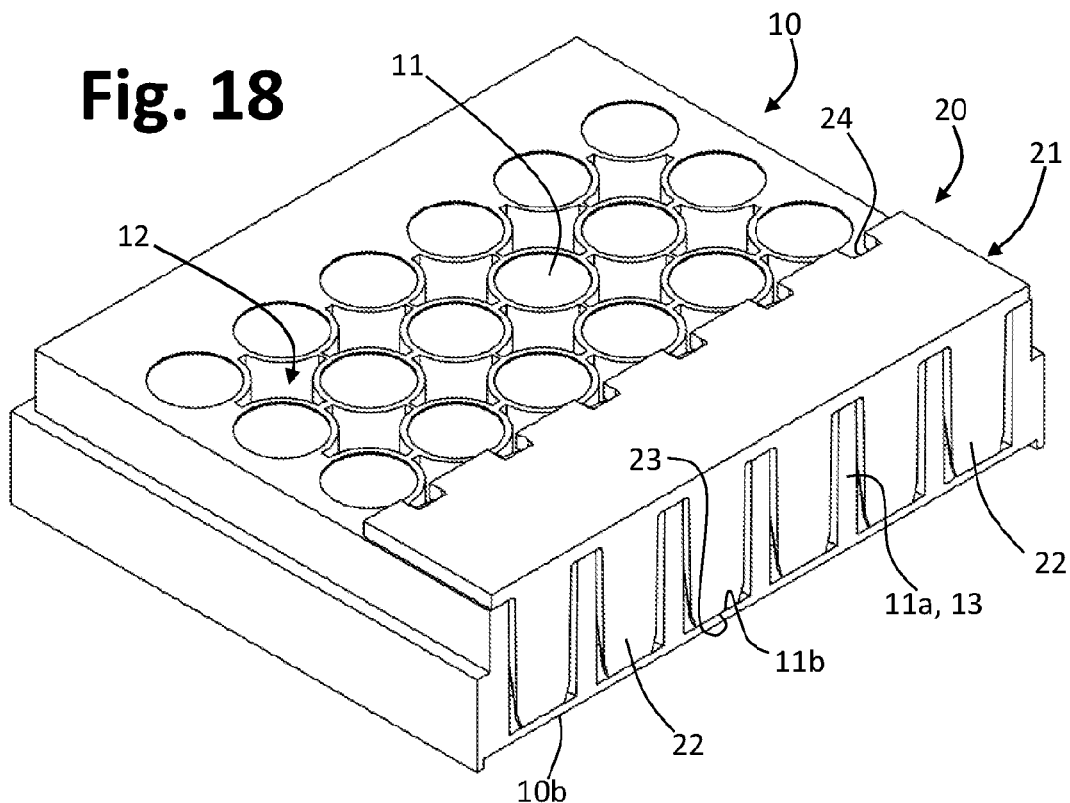

In use, the insert 20 is coupled to the culture plate 10, i.e., set on top of it, in such a way that the exclusion reliefs 22 each fit into a corresponding well 11, with the corresponding distal end 23 that is in contact, with a slight elastic pressure, on the bottom 11b of the well itself, as may be seen, for example, in FIGS. 14-16. The above superimposition step enables the constraint reliefs 25 to fit, with elastic interference, into the corresponding gaps 12 of the plate 10, thereby guaranteeing precision of positioning and the stability of coupling between the insert 20 and the plate 10.

The operation of superimposition/insertion can be performed manually, without the aid of any tool, and is facilitated by the possibility of elastic deformation of the baseplate 21. Following upon this operation, the lower face of the baseplate 21 preferentially adheres to the upper face 10a of the culture plate 10 (i.e., to the top of the sides 10c-10f). Such a condition of preferential coupling is visible, for example, in FIG. 1.

Alternatively, in the lower portion of the baseplate 21 and/or in the upper face 10a of the culture plate 10, reliefs or elements for mutual resting may be provided, in particular for defining a position of resting of the insert 20 with respect to the plate 10, it being consequently possible for the aforesaid reliefs or elements to be set at a distance apart or not totally in contact.

Figure 50:
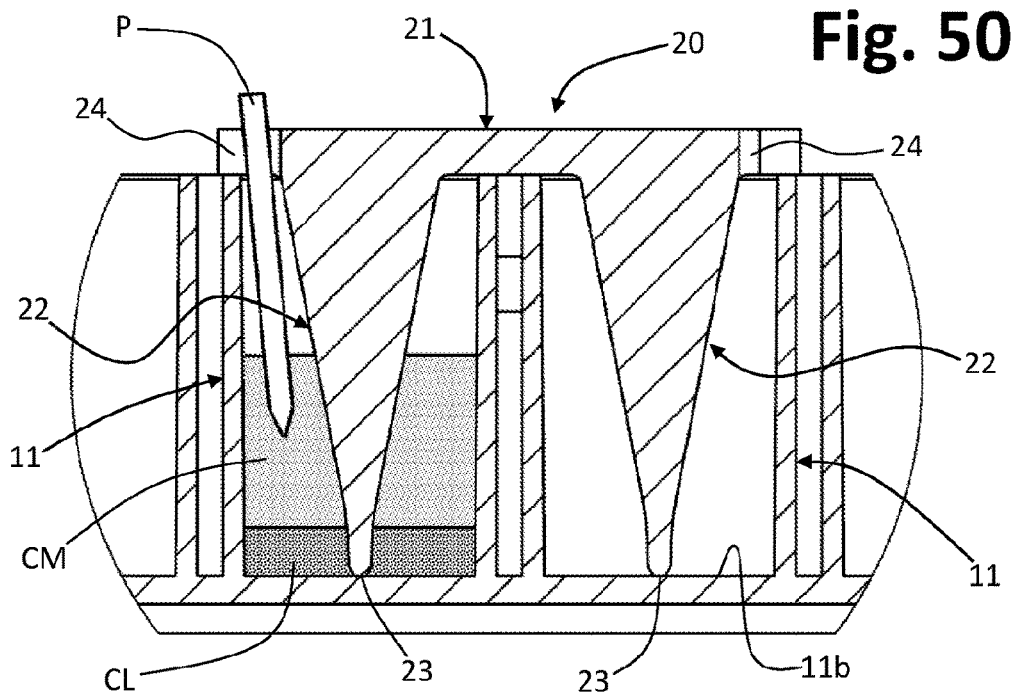
FIG. 50 is a cross-sectional view similar to that of FIG. 15, aimed at exemplifying a possible step of use of a kit that uses a device according to the invention.

Next, by exploiting the presence of the recesses 24 (or openings that replace them), introduced into at least some of the wells 11 occupied by the exclusion reliefs 22 are the cells to be analysed, together with a corresponding culture medium (the culture medium may also be introduced into the wells before or after introduction of the cells). Introduction may be made using a suitable device, as exemplified in FIG. 50, where designated by P is a pipette represented schematically, used for the purpose, inserted through a recess 24. In FIG. 50, CL denotes a cell layer, whereas CM denotes a culture medium. The culture plate 10 with the insert 20 may then be inserted in a purposely provided thermostatic chamber to facilitate cell growth.

The cells hence adhere to the bottom 11b of the well 11, except for the area of the bottom that is in contact with the distal end 23 of the exclusion relief 22. After a certain time, the cells reach confluence—i.e., the corresponding layer CL fills the lower part of the well—except for the area occupied by the distal end portion of the relief 22, as in FIG. 50. This condition is also exemplified in part a) of FIG. 51.

Next, the insert 20 is removed by exerting a tensile force upwards on the baseplate 21, preferably at an edge thereof, thereby causing bending or elastic deformation of the baseplate 21 as it is being moved away from the culture plate 10. The possibility of deformation of the baseplate 21 facilitates removal of the insert 20, which can be performed manually without the aid of any tool. According to a preferential example of removal, the initial part of the step of removal of the insert 20 is exemplified in FIGS. 20-21, where the aforesaid tensile force upwards is exerted at one of the minor edges 21b of the baseplate 21. As may be noted in the figures, for example in FIGS. 22 and 23, in this way elastic deformation of the baseplate 21 is induced, this facilitating the manual operation of removal of the insert 20. The constraint reliefs 25 enable easy detachment of the exclusion reliefs 22 from the bottom surface 11b of the corresponding wells 11 to be obtained during extraction of the insert 20 from the culture plate 10.

Figure 51:
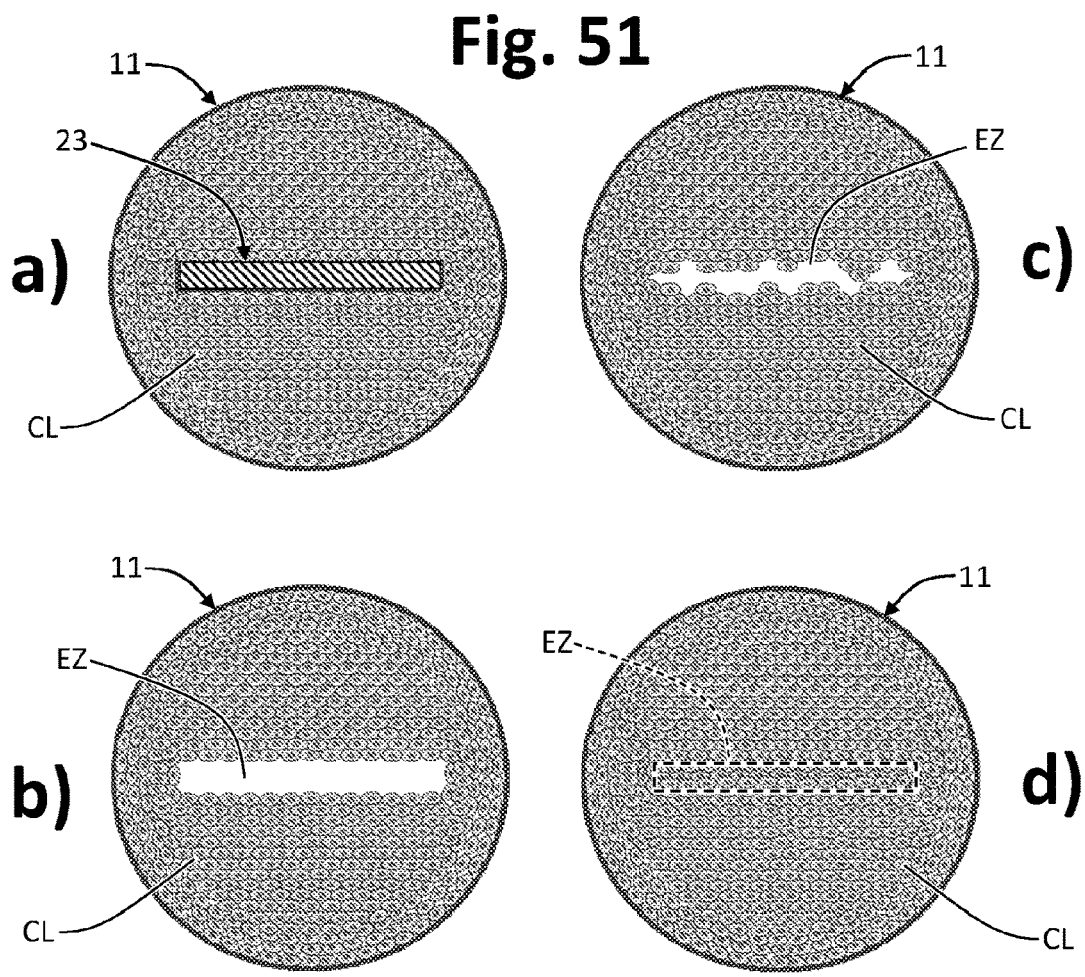
FIG. 51 is a schematic illustration of a possible principle of use of a kit that uses a device according to the invention.

Following upon removal of the insert, in the layers CL of the various wells 11 an exclusion zone is created, i.e., an area free from cells, denoted by EZ in part b) of FIG. 51. The exclusion zone exemplified in part b) of FIG. 51 has a single profile that is substantially elongated and linear, and corresponds substantially to the use of inserts similar to the ones exemplified in FIGS. 1-50. However, as explained hereinafter, the aforesaid profile could be different, according to the shape assigned to the distal end 23 of the relief 22, and/or a relief 22 could have a number of distal ends 23 shaped for defining a plurality of exclusion zones in one and the same well 11.

It will be appreciated that, following upon removal of the insert 20, in the wells 11 of interest cell-exclusion zones EZ are created that have controlled and homogeneous dimensions, and are preferably all aligned in one and the same direction.

Next, migration and/or proliferation of the cells of the layer CL determines progressive occupation of the exclusion zone EZ, up to complete closing thereof, as exemplified in parts c) and d) of FIG. 51, respectively. As explained previously, in this way, it is possible to analyse data of movement and/or proliferation of the cells, for example by acquiring at appropriate time intervals images of the type illustrated in parts b), c), and d) of FIG. 51.

The elongated or oblong shape of the exclusion zone EZ presents the advantage of reducing the time that the cells take to close the area EZ, i.e., of speeding up detection, this also given the same dimensions of the area with respect to a similar exclusion zone of a circular shape in so far as the width or diameter of a circular exclusion zone would be greater than the width of an area EZ of oblong shape according to the present invention.

The elongated or oblong shape of the exclusion zones EZ according to the present invention also makes it possible to provide these zones with angles or directions that are different from one another, albeit in one and the same plate 10 and/or in adjacent wells 11, in this way it being possible to verify also the possible different behaviour of cell growth linked to the different arrangement, for example in the presence of light or heat sources coming from a single direction that impinges differently upon the various exclusion zones EZ.

In various embodiments, the insert 20 has at least two parallel series of exclusion reliefs 22, and the baseplate 21 has a plurality of through openings for access to wells of an underlying multi-well plate. Such a case is exemplified in FIG. 24, which also illustrates a version of insert 20 sized so as to cover the entire culture plate 10, i.e., —with reference to the example—an insert 20 having 48 exclusion reliefs 22 (here not visible).

Figure 24:
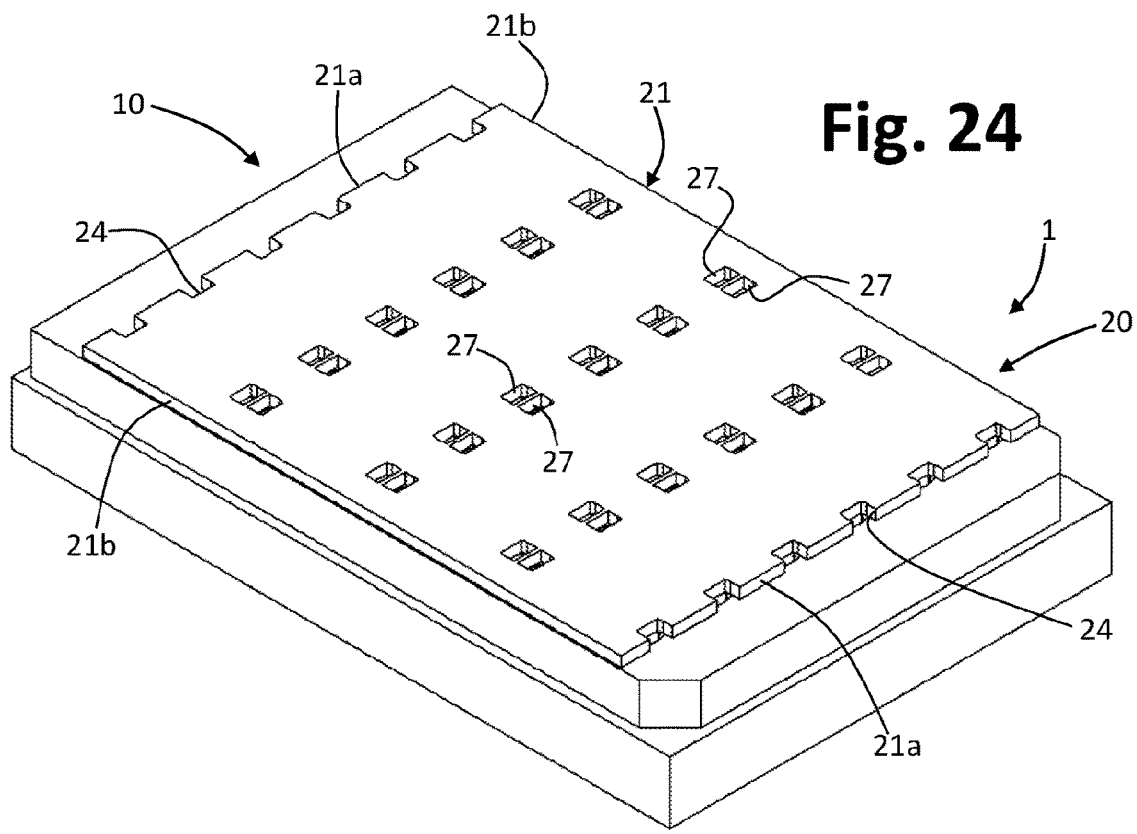
FIG. 24 is a schematic perspective view of a kit that uses a device according to further possible embodiments of the invention.

In the case of FIG. 24, some of the aforesaid through openings—which here have a quadrangular profile—are designated by 27. These openings 27 are defined in a lateral position relative to a respective first exclusion relief. In the example of FIG. 24, the baseplate 21 has six recesses 24 at each of the opposite edges 21a in order to enable access to the wells of the plate 10 closest to the two minor sides of the plate itself. The other 36 wells of the plate 10 are each instead accessible by means of a respective through opening 27.

Illustrated in FIGS. 25-36 are further possible embodiments of the invention, where the insert 20 differs from that of FIGS. 1-24 basically as regards the cross-sectional profile of the exclusion reliefs 22 and as regards the type of through openings of the baseplate 21.

In these embodiments, and as highlighted for example in FIGS. 26, 27, 31, and 34, the two convergent faces of the reliefs 22 are one substantially plane or continuous—designated by $26_3$—and the other distinguished by a number of differently inclined stretches of surface—here three stretches designated by $26_4$, $26_5$, and $26_6$, of which the two end stretches ($26_4$ and $26_6$) have minimum inclination, whereas the intermediate one ($26_5$) has maximum inclination.

Also in these embodiments, it is preferable for the convergent faces of each relief 22 to be shaped so as to extend at least approximately parallel or possibly also modestly inclined with respect to one another, at least in the distal end portion of the relief itself.

The configuration of the reliefs 22 according to the embodiment of FIGS. 25-36 enables reduction of the overall thickness of the reliefs themselves as compared to the embodiments represented in FIGS. 1-24, enabling on the other hand an increase in the dimensions of the passages aimed at allowing access to the wells 11.

In the case of FIGS. 25-36, the aforesaid access passages are all configured as through openings, some of which are designated by $27_1$, which preferentially have a section substantially shaped like a circular segment.

It will be appreciated that, in various embodiments, the baseplate 21 may present, at each exclusion relief 22, at least two through openings $27_1$ in generally opposite lateral positions with respect to the relief itself (it being possible, however, to envisage even just one opening $27_1$ associated to each exclusion relief 22). This characteristic, which may be clearly appreciated, for example, from FIG. 30, facilitates reaching of the inside of the wells 11 after coupling of the insert 20 on the plate 10, making available two access passages $27_1$ for each well in opposite positions. Moreover, thanks to the smaller thickness of the reliefs 22, the section of passage of the openings $27_1$ may be comparatively greater than the one determined by the recesses 24 or by the openings 27 of the embodiments represented in FIGS. 1-24.

Figure 37:
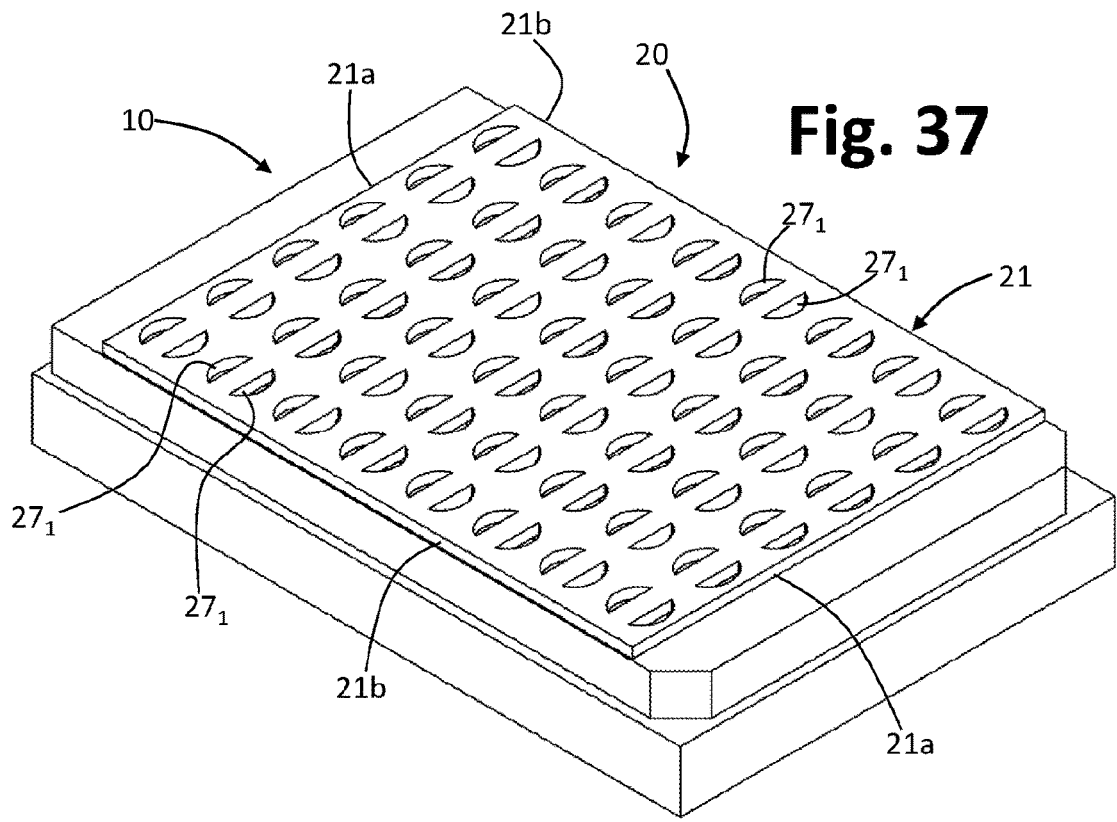
FIG. 37 is a schematic perspective view of a kit that uses a device according to further possible embodiments of the invention.
Figure 38:
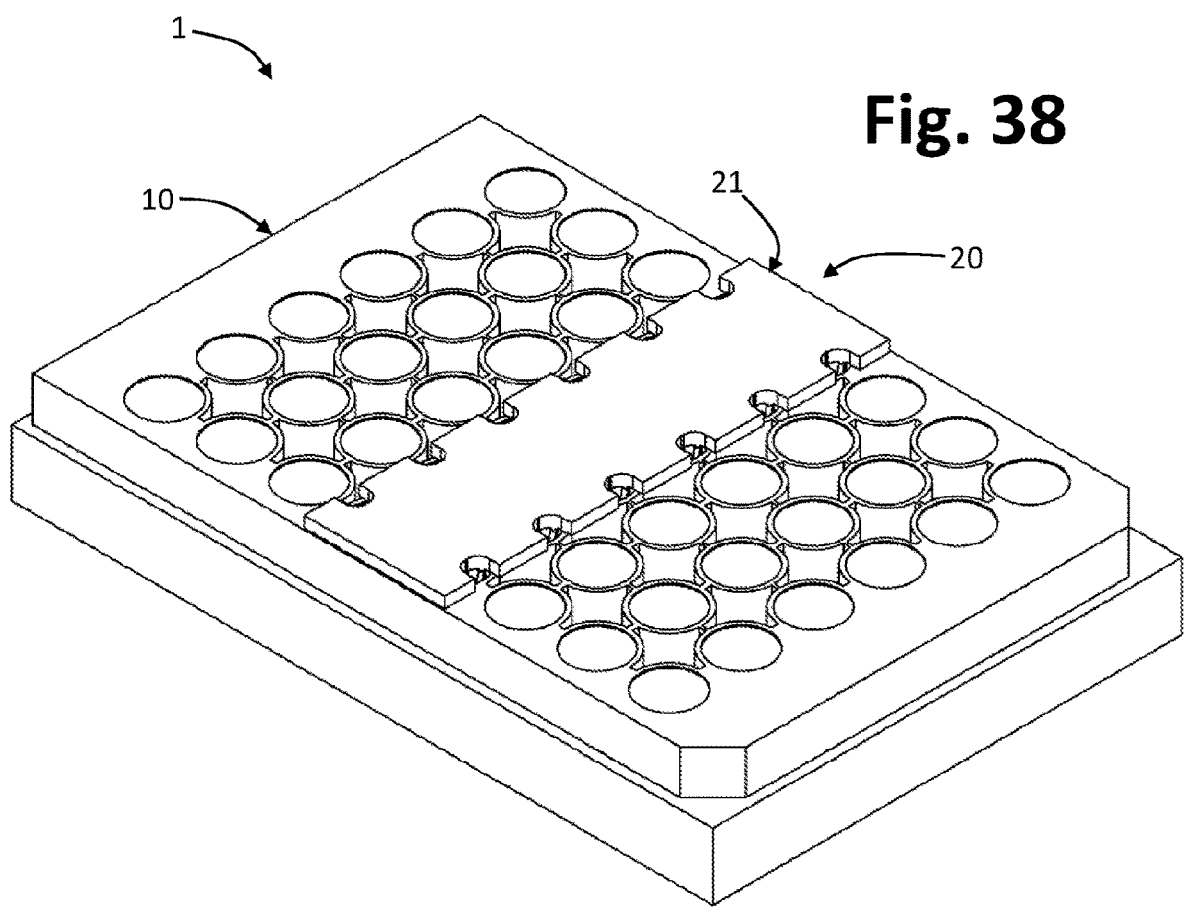
FIG. 38 is a schematic perspective view of a kit that uses a device according to further possible embodiments of the invention.
Figure 39:
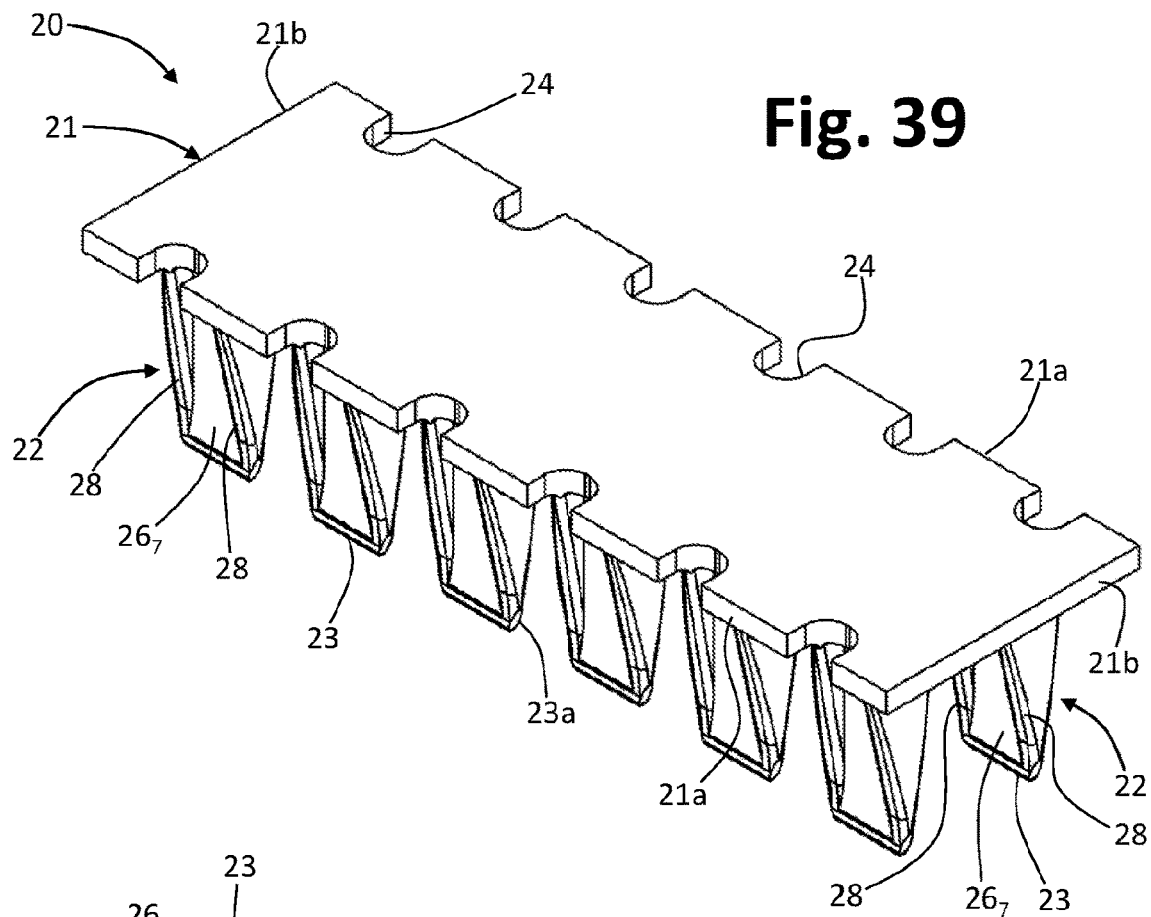
FIGS. 39 and 40 are schematic perspective views from different angles of a device of the kit of FIG. 38.
Figure 40:
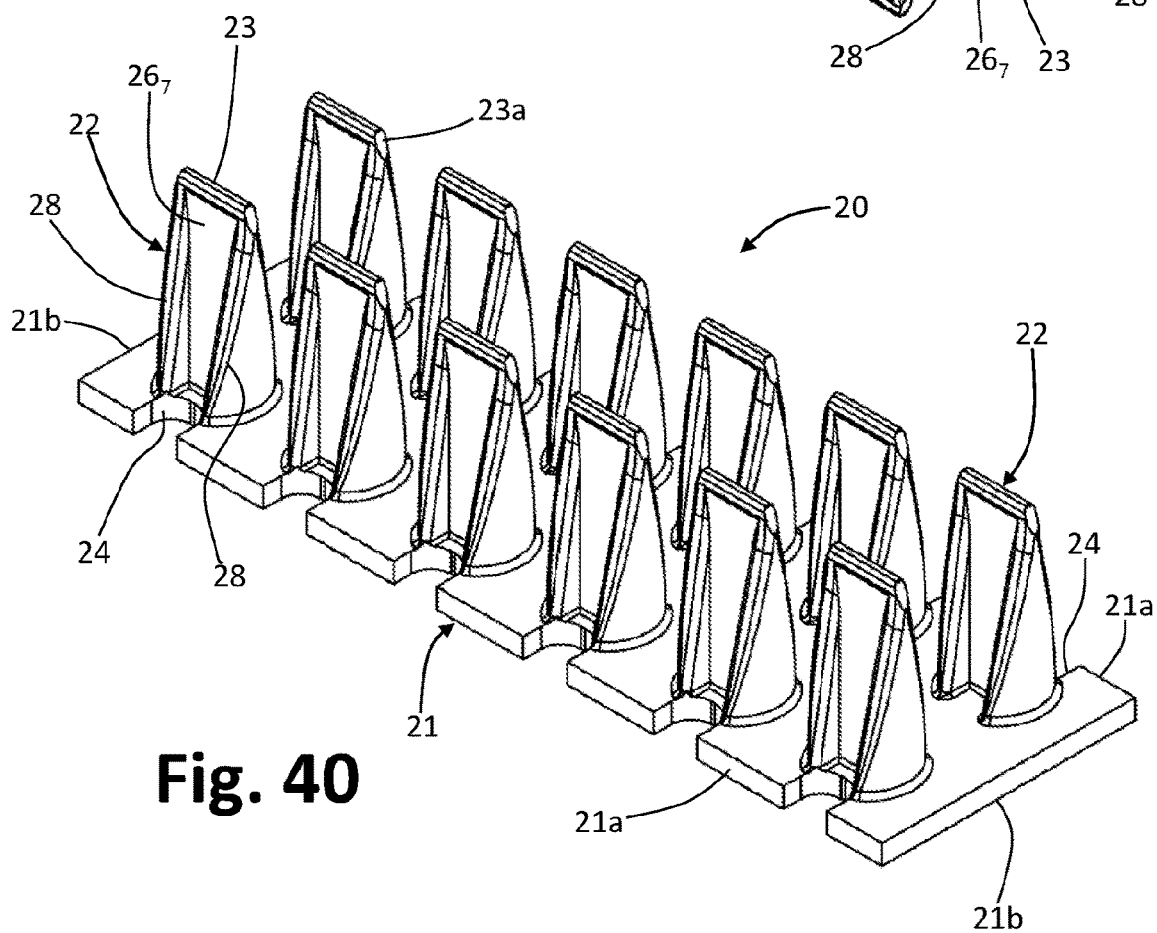
Figure 41:
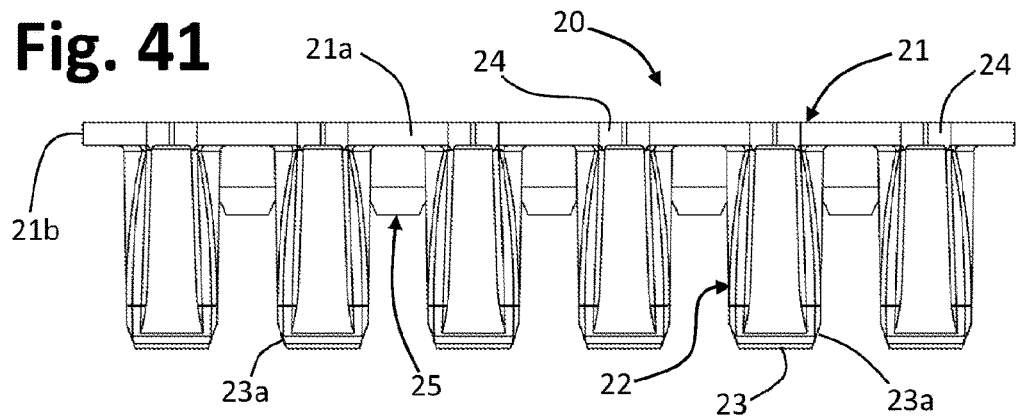
FIGS. 41, 42, 43, and 44 are schematic views, in side elevation, from above, from beneath, and in front elevation, respectively, of the device of FIGS. 39-40.
Figure 42:
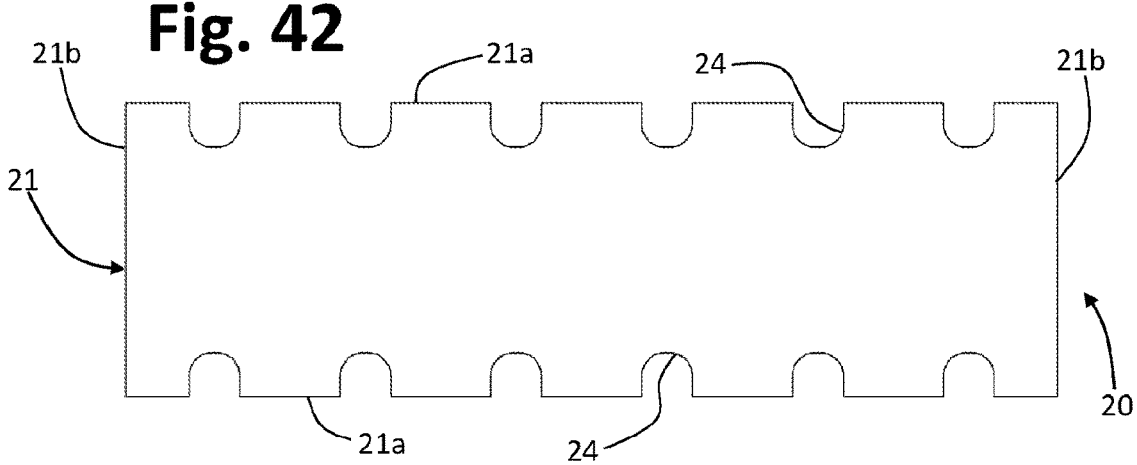
Figure 43:
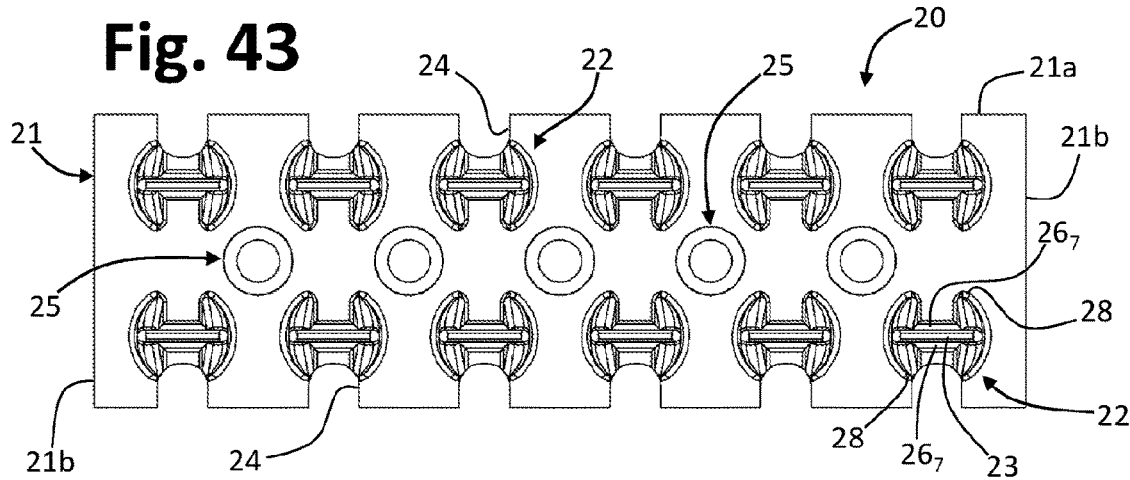
Figure 44:
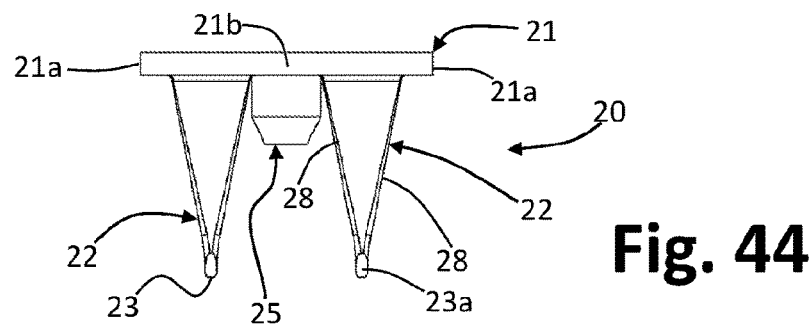
Figure 45:
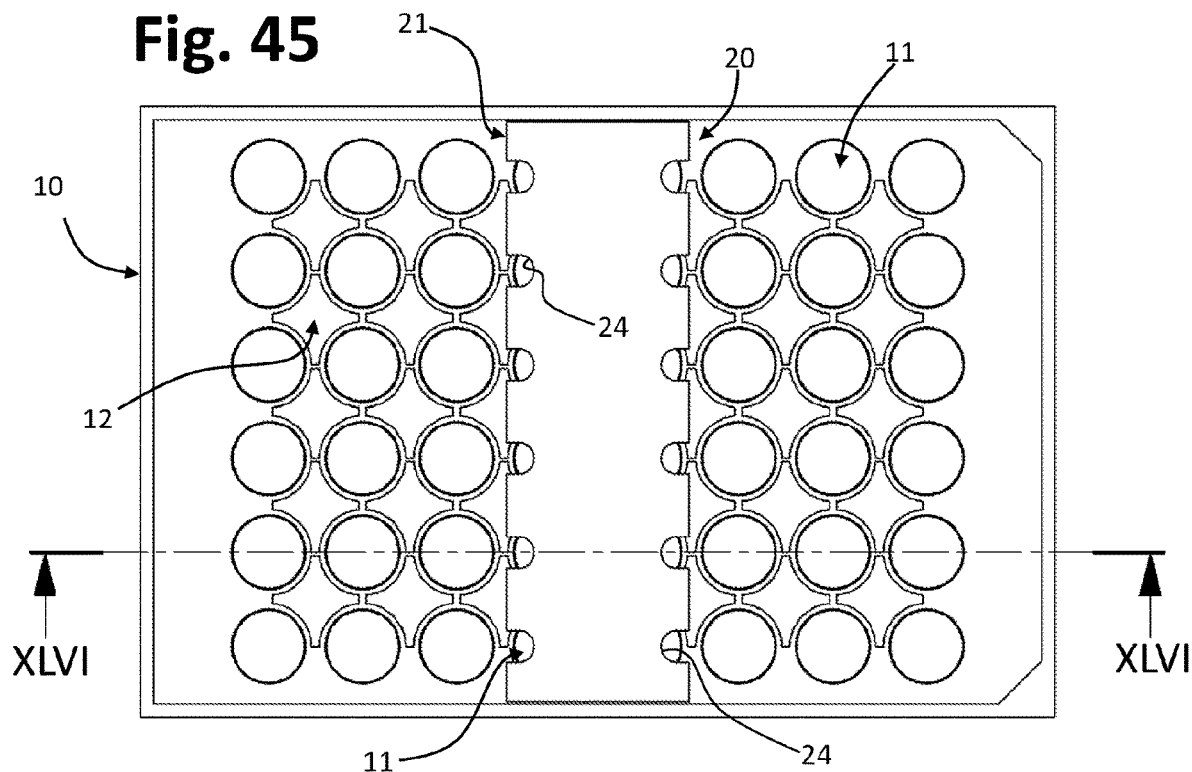
FIG. 45 is a schematic top plan view of the kit of FIG. 38.
Figure 46:
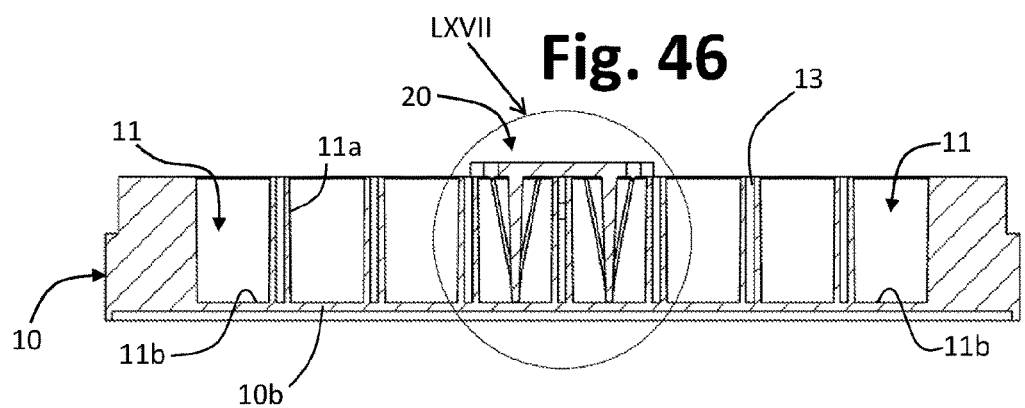
FIG. 46 is a schematic cross-sectional view according to the line XLVI-XLVI of FIG. 45.

As may be appreciated, the modalities of use of the insert 20 of FIGS. 25-36 are similar to those described with reference to FIGS. 1-24. FIG. 37 exemplifies a case similar to that of FIG. 24, i.e., an insert 20 sized so as to cover the entire culture plate 10, in particular having 48 exclusion reliefs 22 (here not visible). In the example, 96 through openings $27_1$ are hence provided.

In the cases illustrated in FIGS. 25-37, the recesses 24 of FIGS. 1-24 are not envisaged, but obviously there is nothing to rule out providing similar recesses at the opposite edges 21a of the baseplate 21 of the insert 20 (in which case the openings $27_1$ closest to these edges could be omitted).

FIGS. 38-49 illustrate further possible embodiments of the invention, where the insert 20 differs from that of FIGS. 1-24 basically as regards the cross-sectional profile of the exclusion reliefs 22 and as regards the shape of the recesses 24, here having an approximately semicircular profile (these possibly also being, however, through openings, for example with a circular closed profile).

Figure 47:
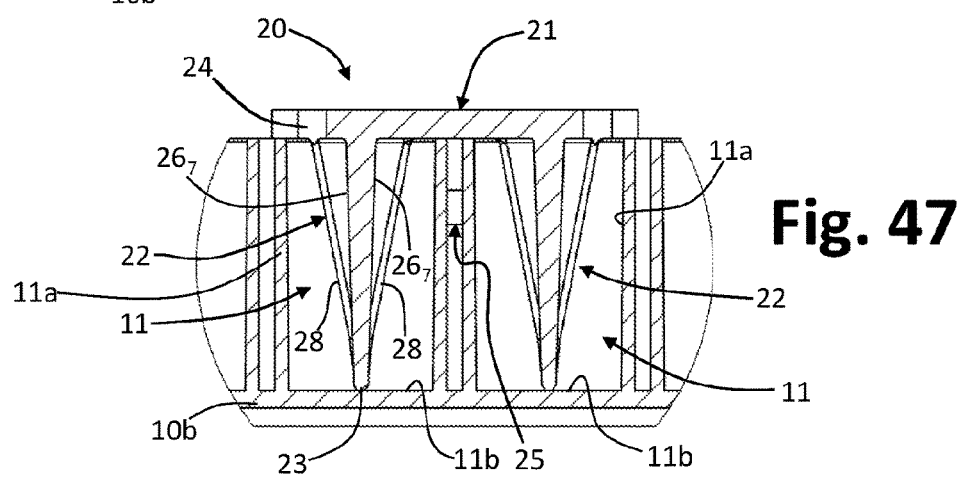
FIG. 47 illustrates the detail XLVII of FIG. 46.
Figure 48:
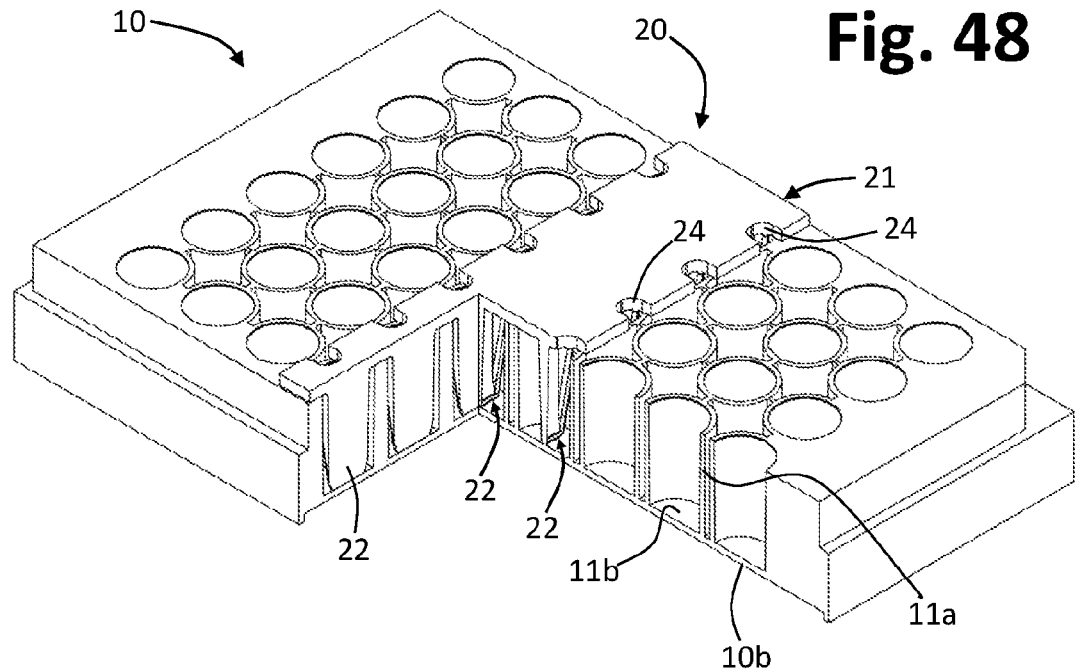
FIGS. 48 and 49 are sectioned perspective views of the kit of FIG. 38.
Figure 49:
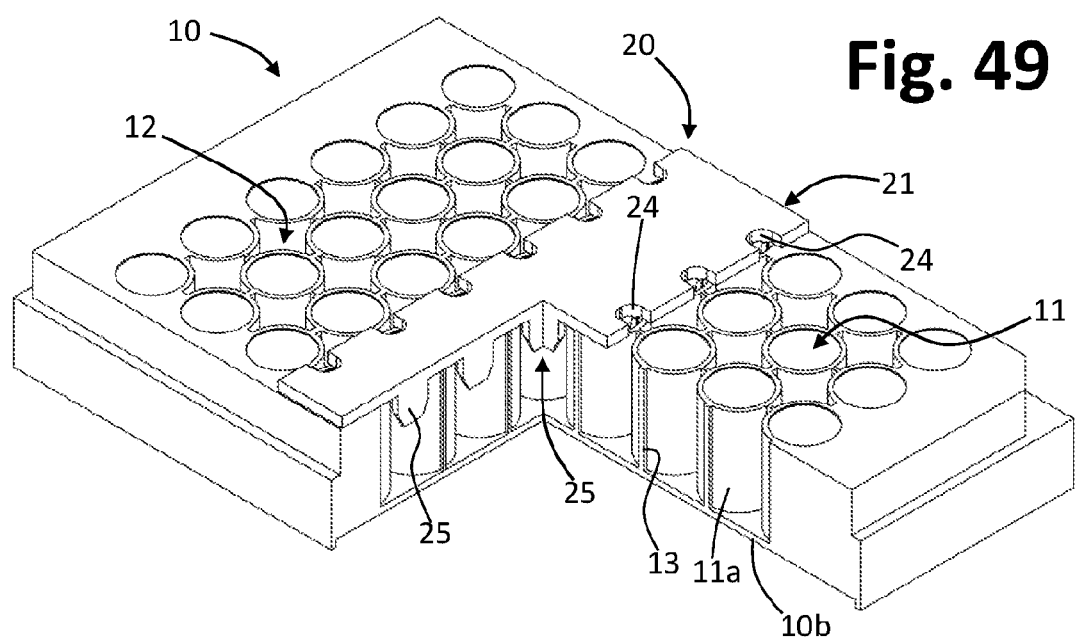

In embodiments of the type represented in FIGS. 38-49, the exclusion reliefs 22 have a structure substantially shaped like a lamella, i.e., distinguished by a small thickness, with the two opposite major faces of the lamella that preferentially converge with respect to one another with a very modest inclination, as clearly visible, for example, in FIG. 47, where the opposite major faces of the lamellar relief 22 are designated by $26_7$.

In these embodiments, it is preferable to provide the lamellar reliefs 22 with stiffening ribbings, in order to bestow upon the reliefs themselves 22 a sufficient structural stiffness. In the case illustrated, ribbings are provided, designated, for example, by 28 in FIGS. 39-40, 43-44, and 47, preferably configured as substantially orthogonal longitudinal edges or ribs of the lamellar relief 22 (it being possible, however, for them to be ribbings located in another position, such as ribs that are intermediate with respect to the lamellar relief 22). In the example considered the ribbings or edges 28 have an arched profile, but evidently this does not constitute an essential characteristic.

Also the modalities of use of the insert 20 of FIGS. 38-49 are similar to those described with reference to FIGS. 1-23. Of course, also the insert 20 of FIGS. 38-49 can be sized as illustrated in FIG. 24.

Figure 52:
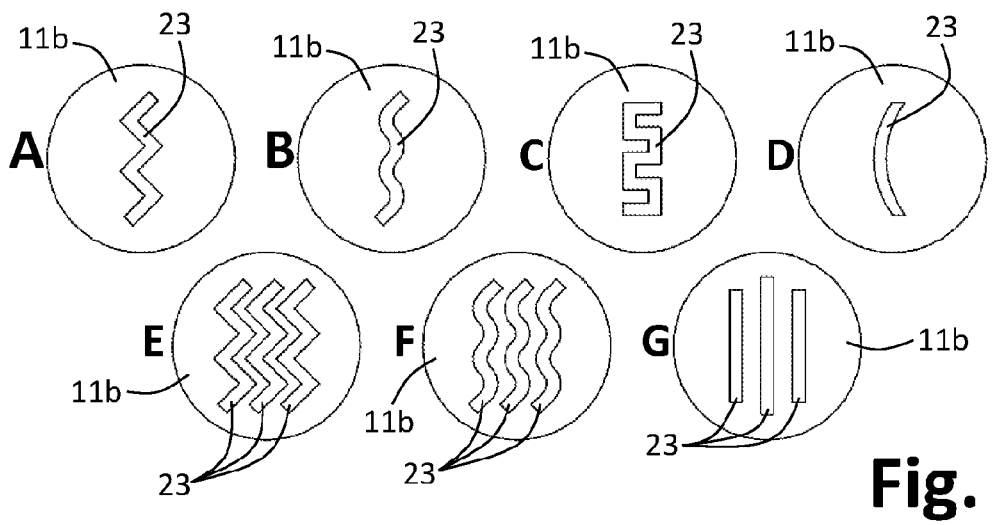
FIGS. 52, 53, and 54 are schematic illustrations of possible variant embodiments of the invention.

As has been mentioned previously, the profile and/or number of the exclusion zones associated to a relief 22, and/or the orientation of the ends of a number of reliefs 22, may differ from what has been exemplified previously. In FIG. 52, some possible variants in this sense are highlighted schematically, via the representation of the bottom 11b of a single well and the distal end 23 (or ends 23) of a corresponding exclusion relief, having a generally elongated shape.

Part a) of FIG. 52 highlights the case of an end 23 the profile of which is represented by a succession of angled linear stretches, i.e., substantially having the shape of a zig-zag, whereas part b) of the same figure highlights the case of an end 23 with a sinuous profile, i.e., distinguished by a plurality of curves in opposite directions. Parts c) and d) of FIG. 52 highlight, instead, ends 23 with a fretted profile and an as a whole curved profile, respectively. According to variants (not represented), the profile could be represented by a succession or combination of linear stretches and/or curves also having shapes and/or lengths different from one another.

Parts e), f), and g) of FIG. 52 highlight, instead, the case of an exclusion relief defining a plurality of ends 23, here set alongside one another or substantially parallel to one another or equidistant: in the case of parts e) and f) of FIG. 52 a plurality of ends 23 are provided of the types represented in parts a) and b) of the same figure, substantially of equal length and parallel to one another. In the case of part g) of FIG. 52, the ends 23, albeit substantially parallel to one another, are of different length, in particular with a longer central end 23 and two shorter side ends 23.

Figure 53:
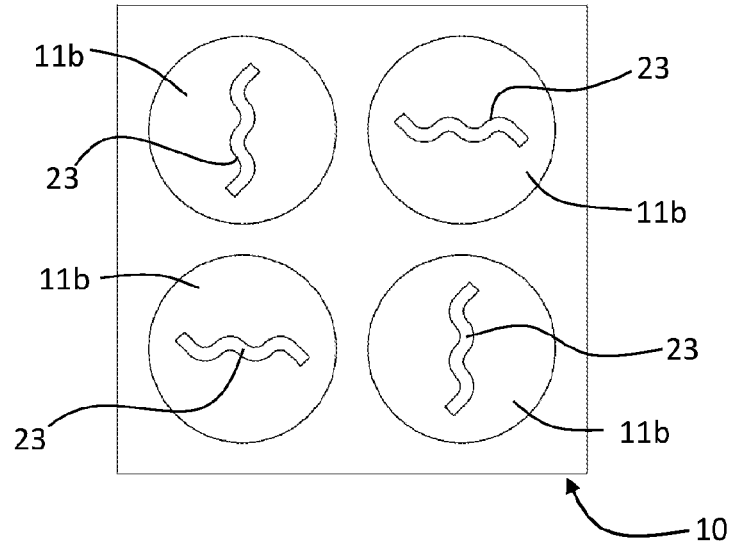
Figure 54:
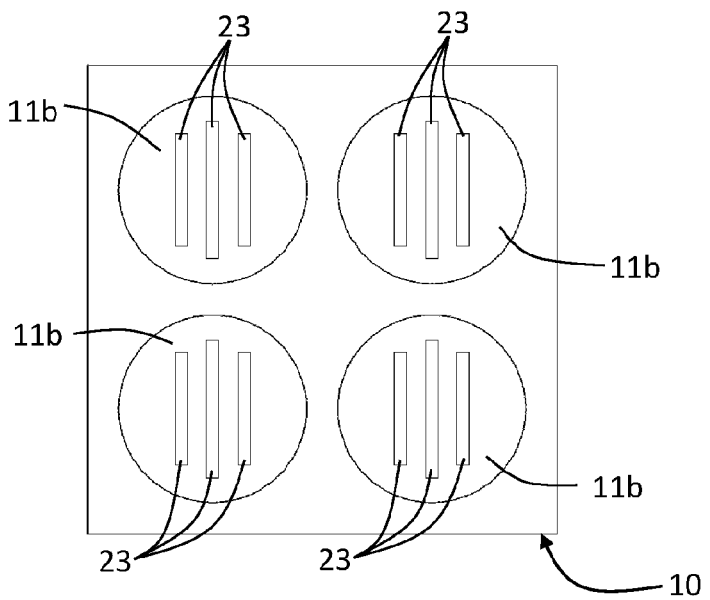
Figure 55:
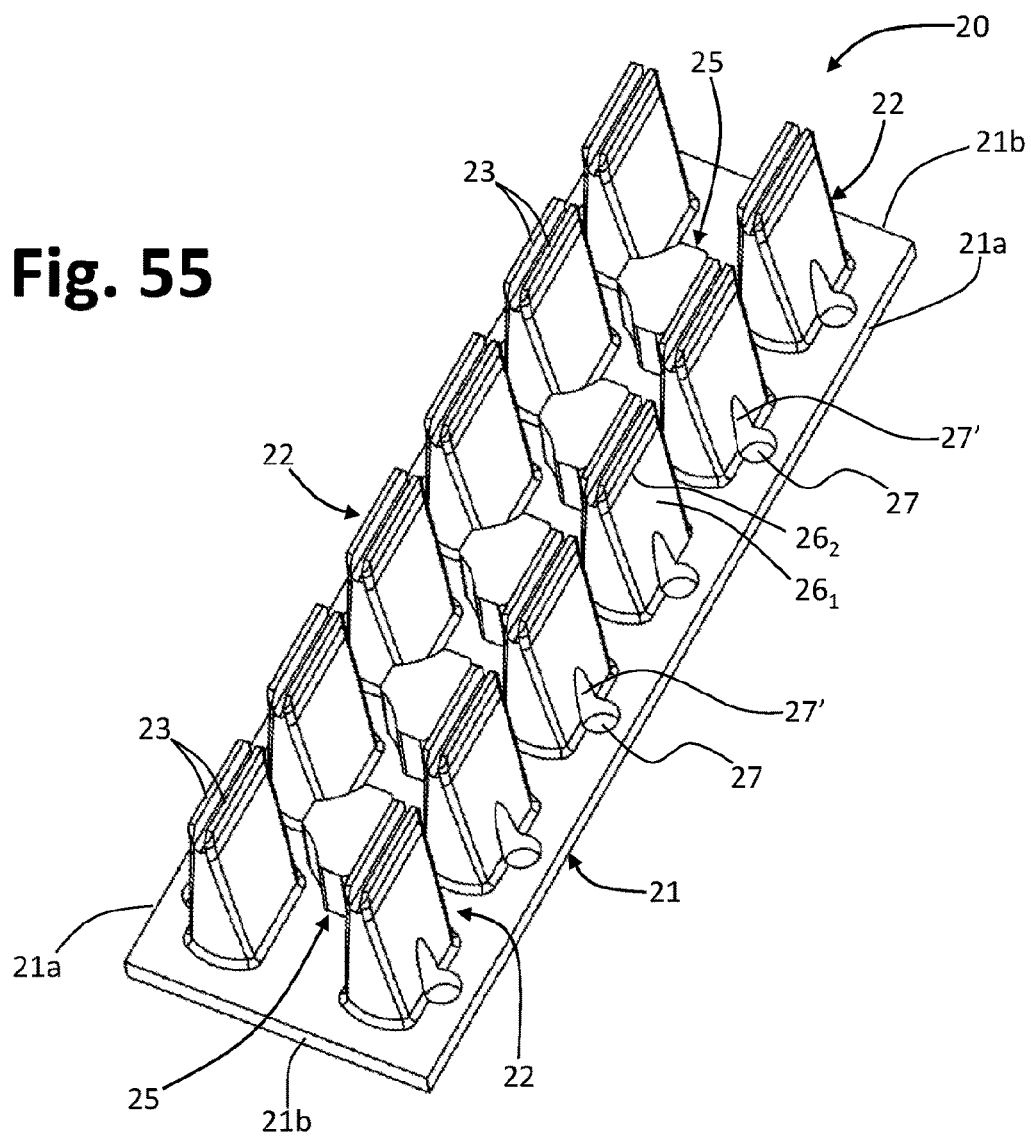
FIGS. 55-59 are views similar to those of FIGS. 6-10, of a device according to further possible embodiments of the invention.
Figure 56:
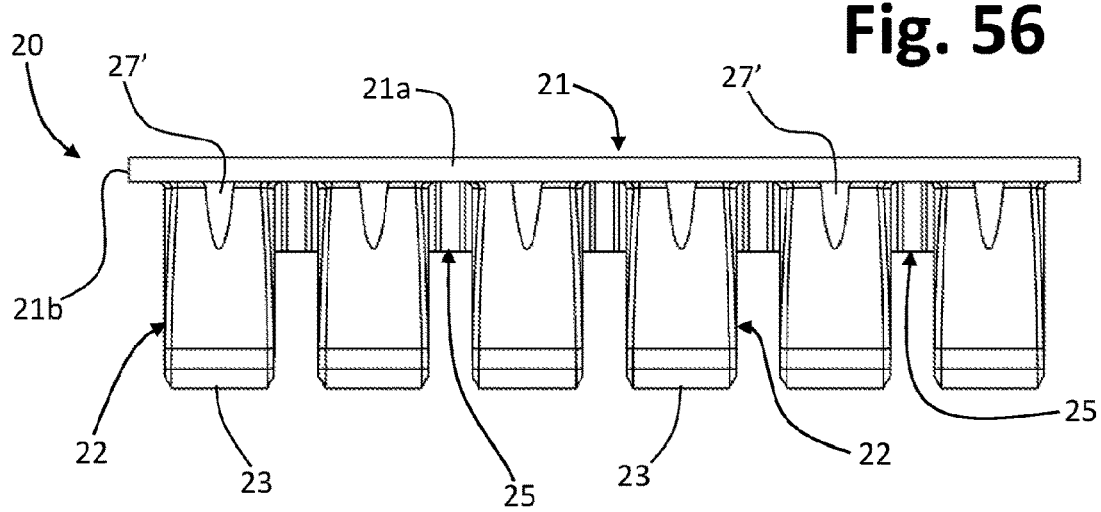
Figure 57:
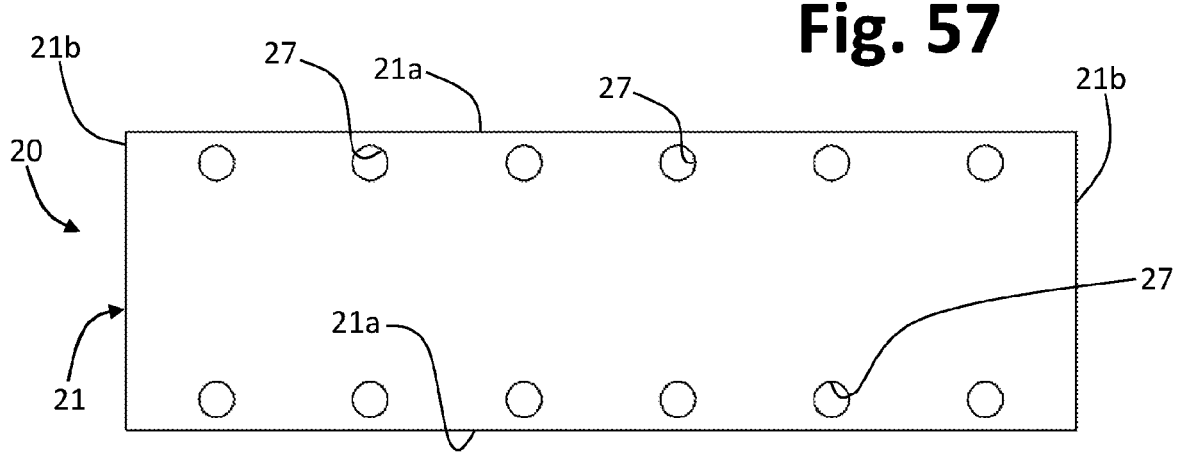
Figure 58:
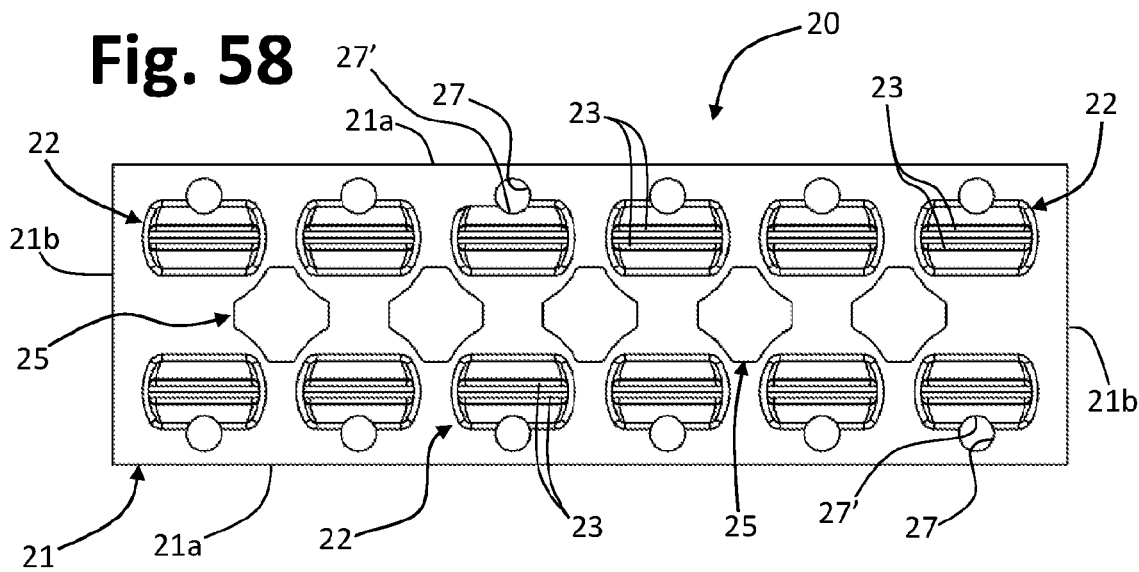
Figure 59:
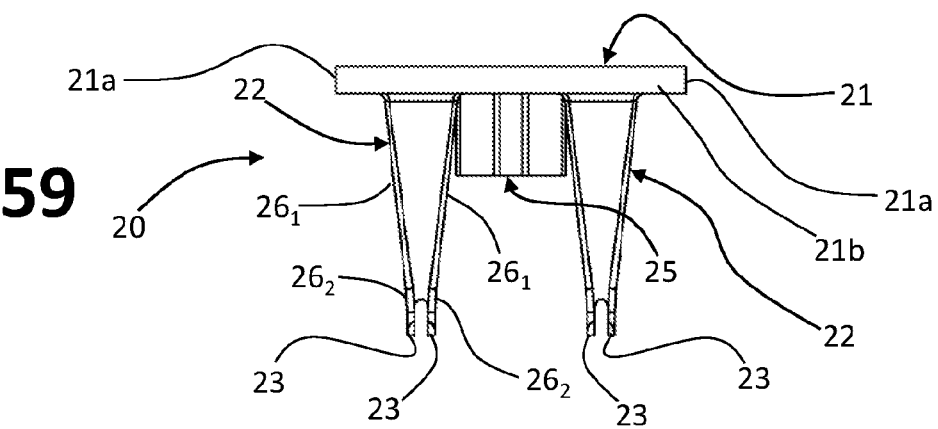

FIG. 53 highlights the case of four exclusion reliefs with single end 23 (of the type illustrated in part b) of FIG. 52), which are oriented in a different way with respect to one another, whereas FIG. 54 illustrates the case of four exclusion reliefs, each of which has three ends 23 that are generally parallel (of the type illustrated in part g) of FIG. 52) and are oriented in the same direction. At least two of the reliefs described with reference to FIG. 52 could be combined together and/or oriented in the same direction or in directions different from one another, also with angles different from the ones represented by way of example with reference to FIG. 53, i.e., with an orientation in which they are not necessarily mutually orthogonal.

FIGS. 55-59 illustrate further possible embodiments of the invention, where the insert 20 differs from that of the previous figures chiefly as regards the fact that the exclusion reliefs 22 each have a pair of distal ends with oblong profile, generally parallel to one another, as regards the shape of the through openings 27, here substantially circular, and as regards the shape of the constraint reliefs 25.

Also in embodiments of the type represented in FIGS. 55-59, the exclusion reliefs 22 can have a substantially wedge-shaped or lamella-shaped structure, the bottom part of which (with respect to the baseplate 21) is shaped so as to define at least two distal ends 23, which have a generally oblong profile and are preferably substantially of the same length and parallel to one another. In the example represented, the ends 23 have a substantially straight profile, but they could be shaped in various ways, for example according to what has been described with reference to FIGS. 52-54.

In the case exemplified, the constraint reliefs 25 have a shape substantially complementary to that of the gaps 12; i.e., they have an outer profile with a substantially astroid-shaped cross section, preferably with a profile of the reliefs 25 of dimensions at least in part slightly larger than the profile of the gaps 12, in particular for insertion with at least slight elastic interference into the gaps 12. As has been mentioned, in this case, the through openings 27 have a circular shape.

FIGS. 55-59 illustrate also possible embodiments, where the baseplate 21 is provided with openings 27 that have a circular profile. These circular openings 27 may have a diameter close to, similar to, or slightly smaller than the diameter of an instrument, such as a serological pipette, in particular of the type designed to be at least in part inserted in a well 11 or rested at the aforesaid openings 27 or at the well 11. The elastic characteristics of the material that forms the baseplate 21 and/or that defines or surrounds the openings 27 contributes to reducing the risk of accidental breaking of the instrument, which is frequently made of glass and is hence very brittle, and/or enables provision of a seal around the instrument.

In various embodiments, defined on at least one of the two convergent sides of each relief 22 is a recess or groove axially aligned to a corresponding opening 27 of the baseplate 21. Some of these recesses are designated by 27' for example in FIGS. 55, 56 and 58. The presence of the recess 27' facilitates insertion into a corresponding well 11 of an instrument, such as a serological pipette, likewise contributing to reducing the risk of accidental breaking thereof.

Figure 25:
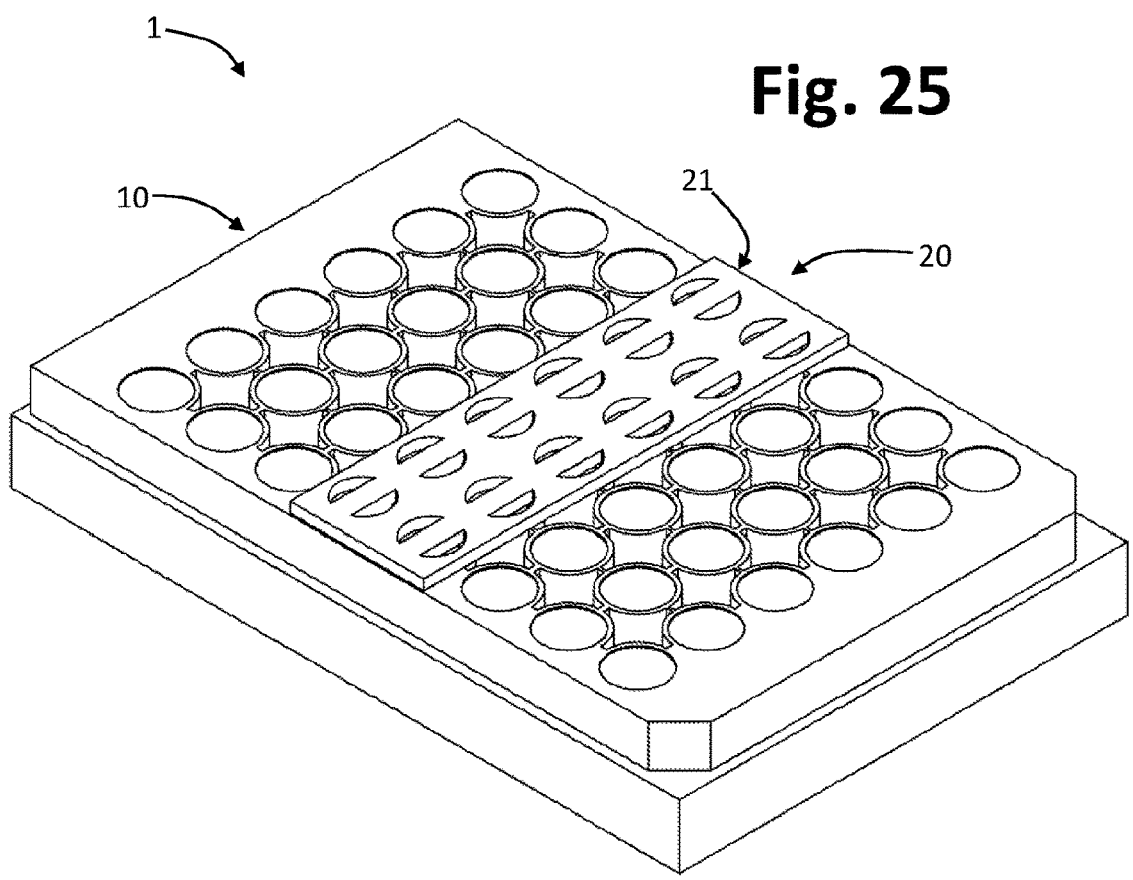
FIG. 25 is a schematic perspective view of a kit that uses a device according to further possible embodiments of the invention.
Figure 26:
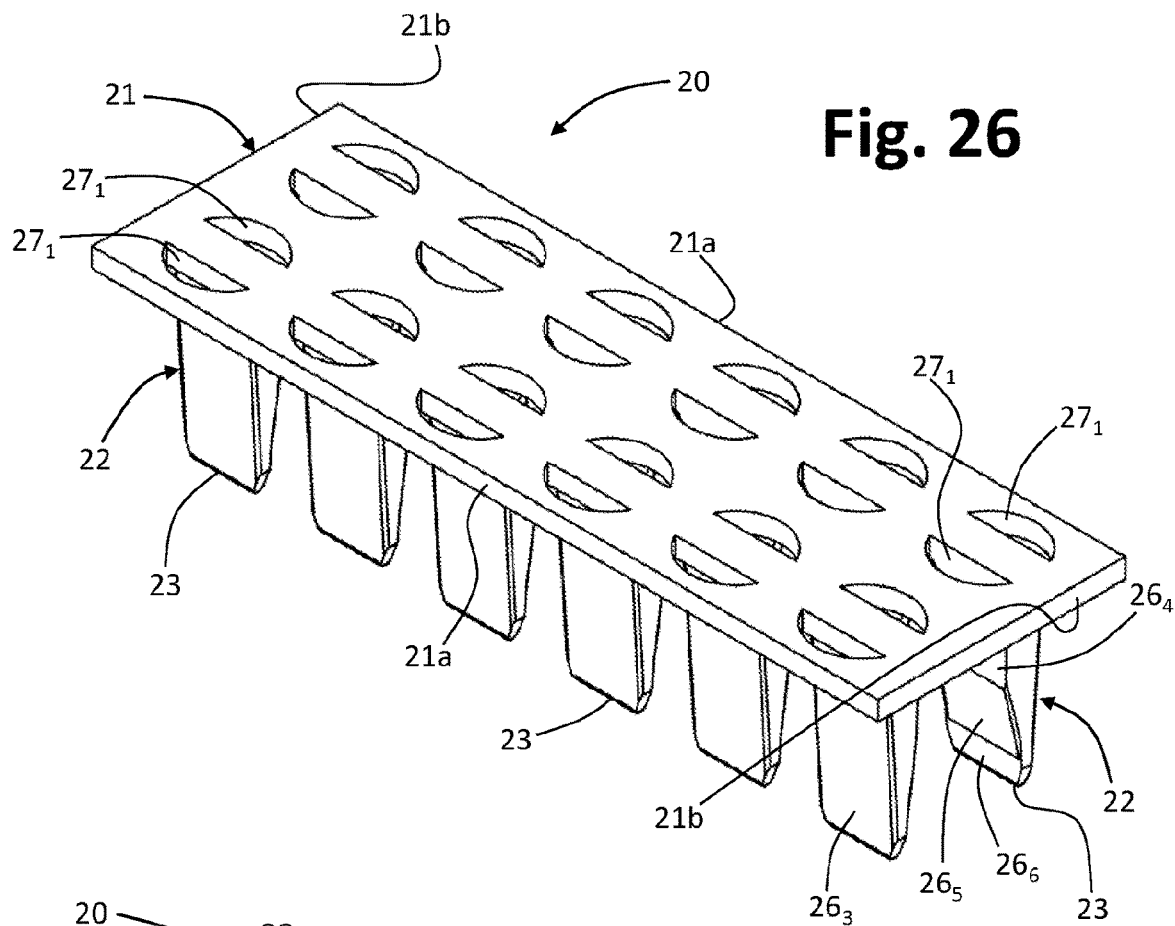
FIGS. 26 and 27 are schematic perspective views, from different angles, of a device of the kit of FIG. 25.
Figure 27:
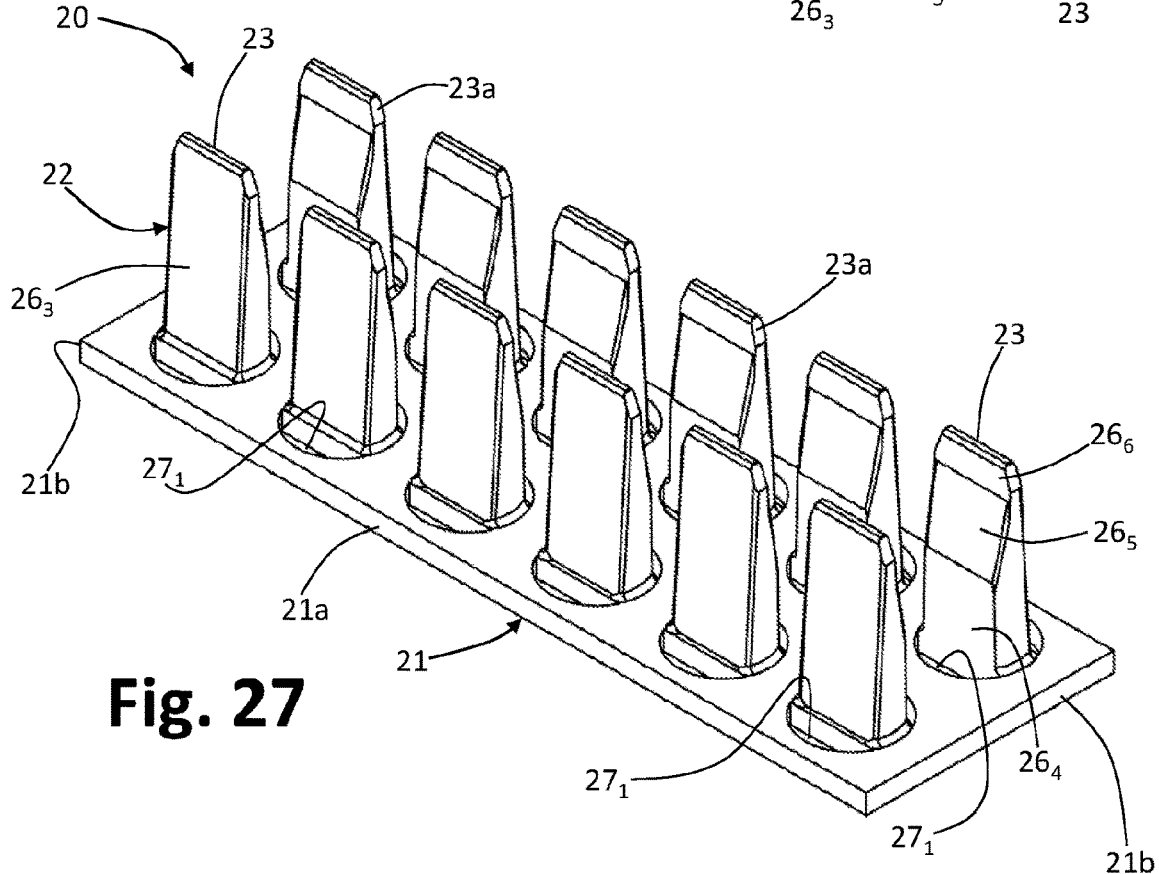
Figure 32:
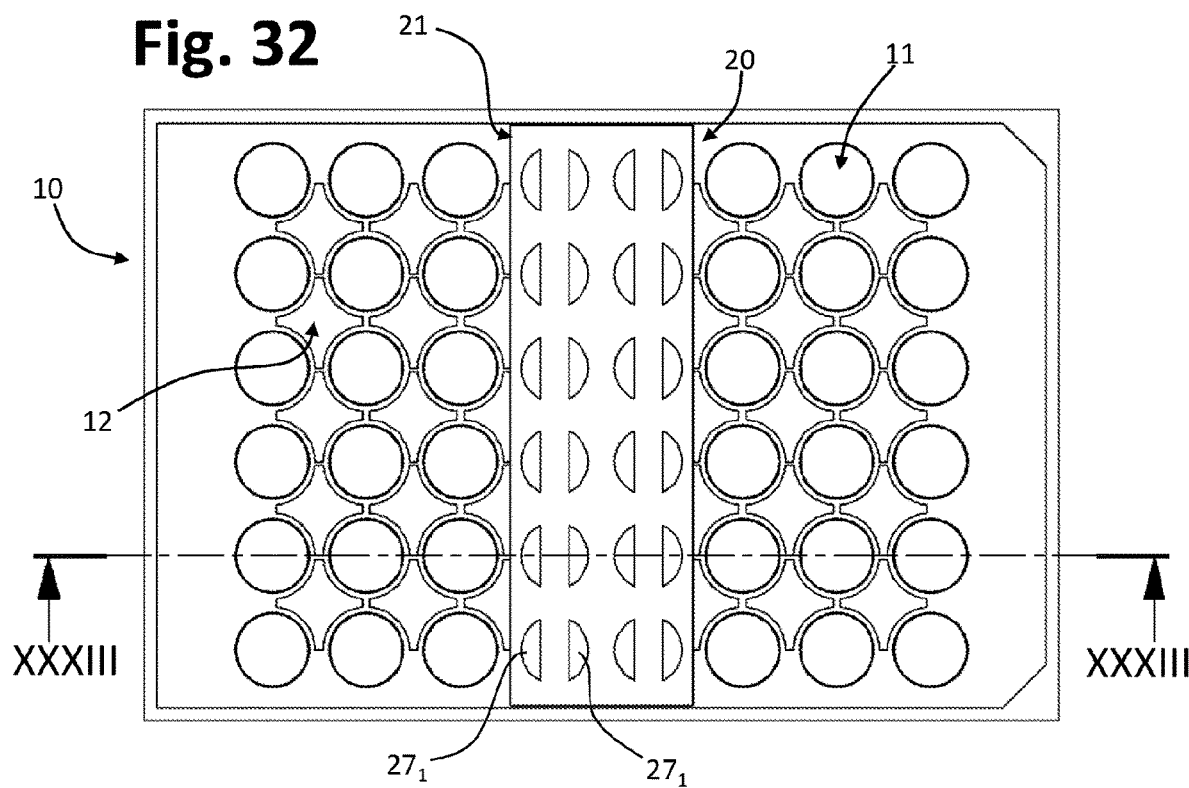
FIG. 32 is a schematic top plan view of the kit of FIG. 25.
Figure 33:
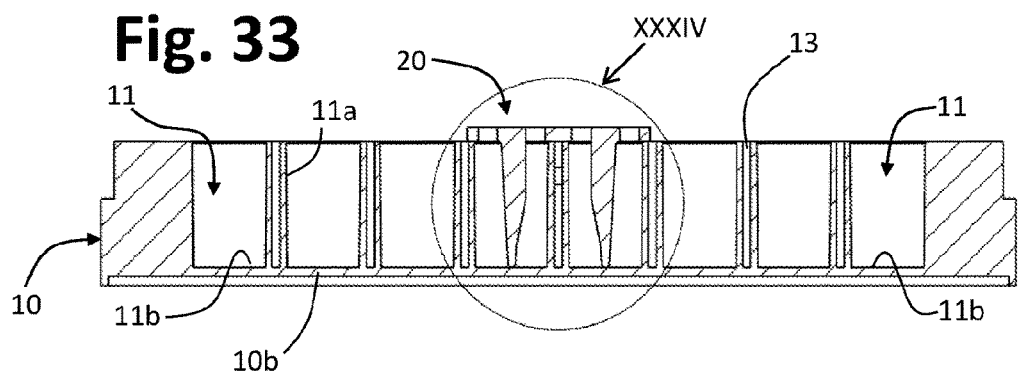
FIG. 33 is a schematic cross-sectional view according to the line XXXIII-XXXIII of FIG. 32.
Figure 34:
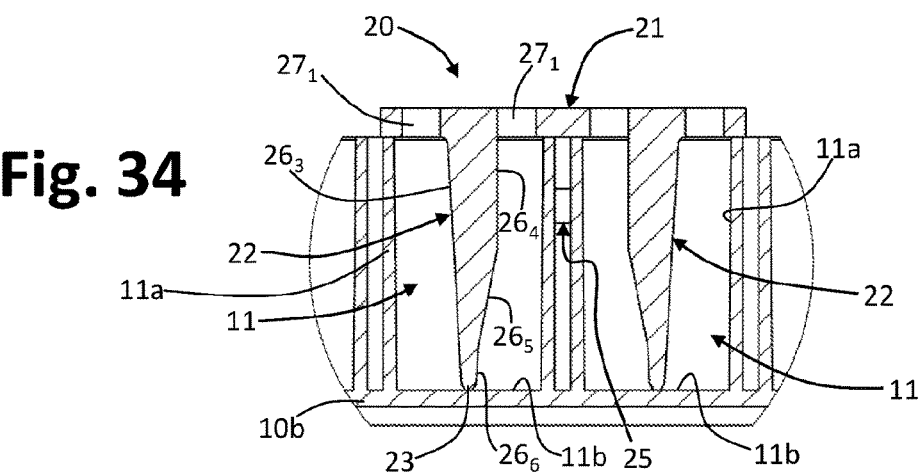
FIG. 34 illustrates the detail XXXIV of FIG. 33 at a larger scale.
Figure 35:
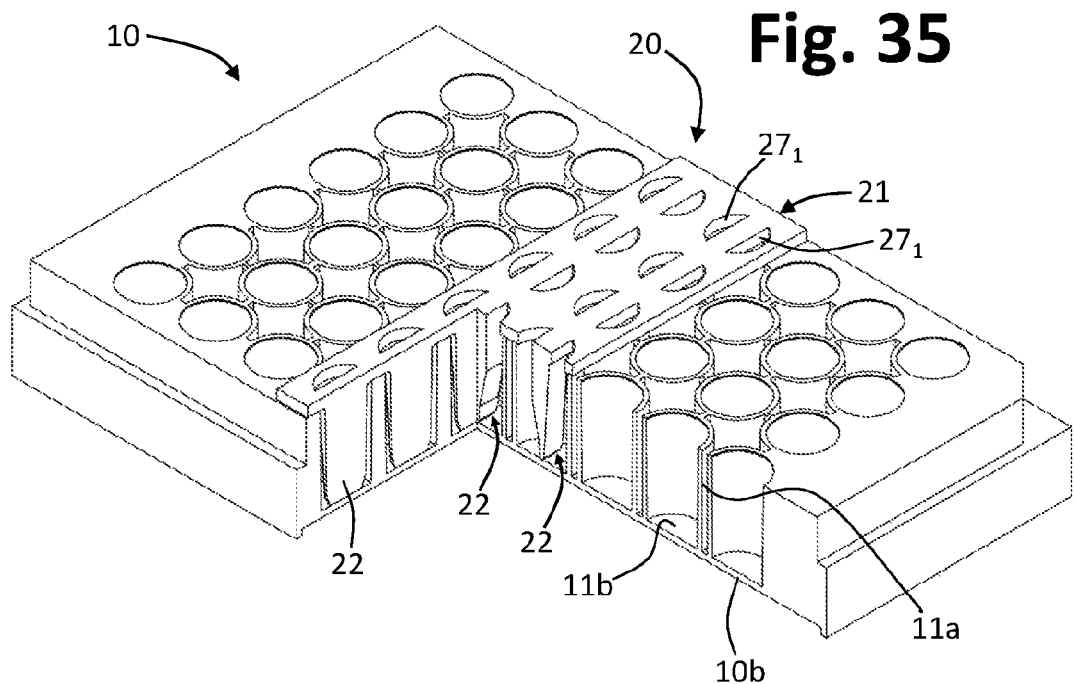
FIGS. 35 and 36 are sectioned perspective views of the kit of FIG. 25.
Figure 36:
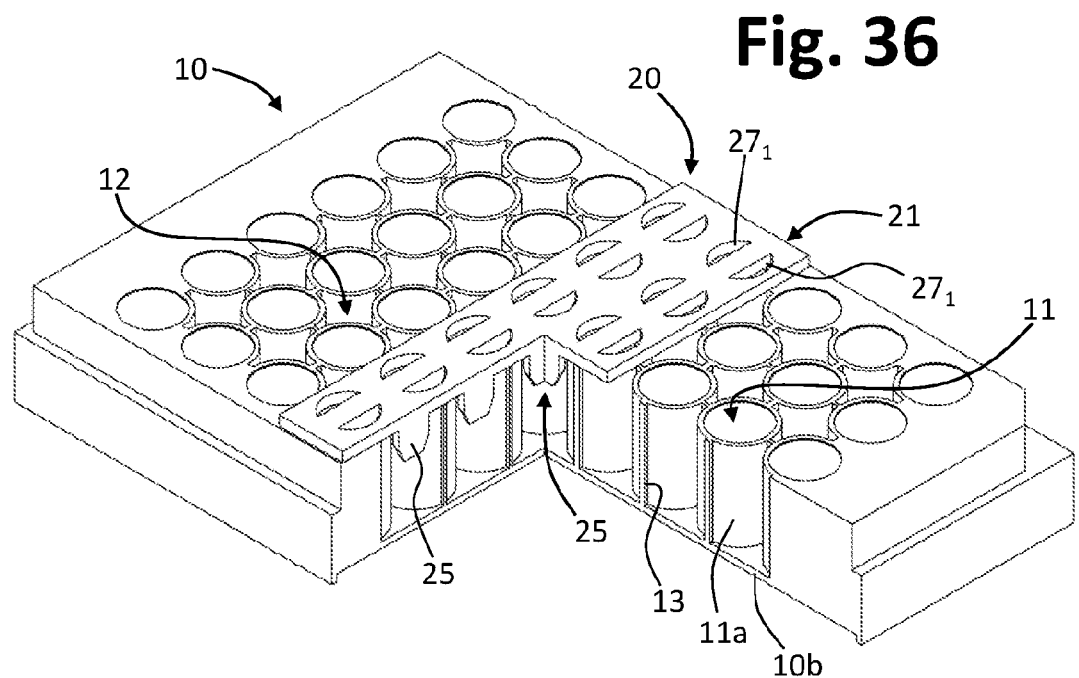

The modalities of use of the insert 20 of FIGS. 55-59 are substantially similar to those described with reference to FIGS. 1-24, with the difference that, in this case, in each well 11 two exclusion zones will be defined, each by a respective end 23 of the reliefs 22. As has been mentioned previously, this may prove useful for the purposes of analysis. Of course, also the insert 20 of FIGS. 55-59 can be variously sized, for example as illustrated in FIG. 25.

FIGS. 60-66 are a schematic illustration of possible use of an insert 20 according to FIGS. 55-59 (however, they may also refer to inserts with different shapes, such as inserts according to FIGS. 1-54). The above figures illustrate also possible embodiments in which the culture plate 10 has a bottom of an "active" type, i.e., provided with sensor means for detection of analysis variables.

Figure 60:
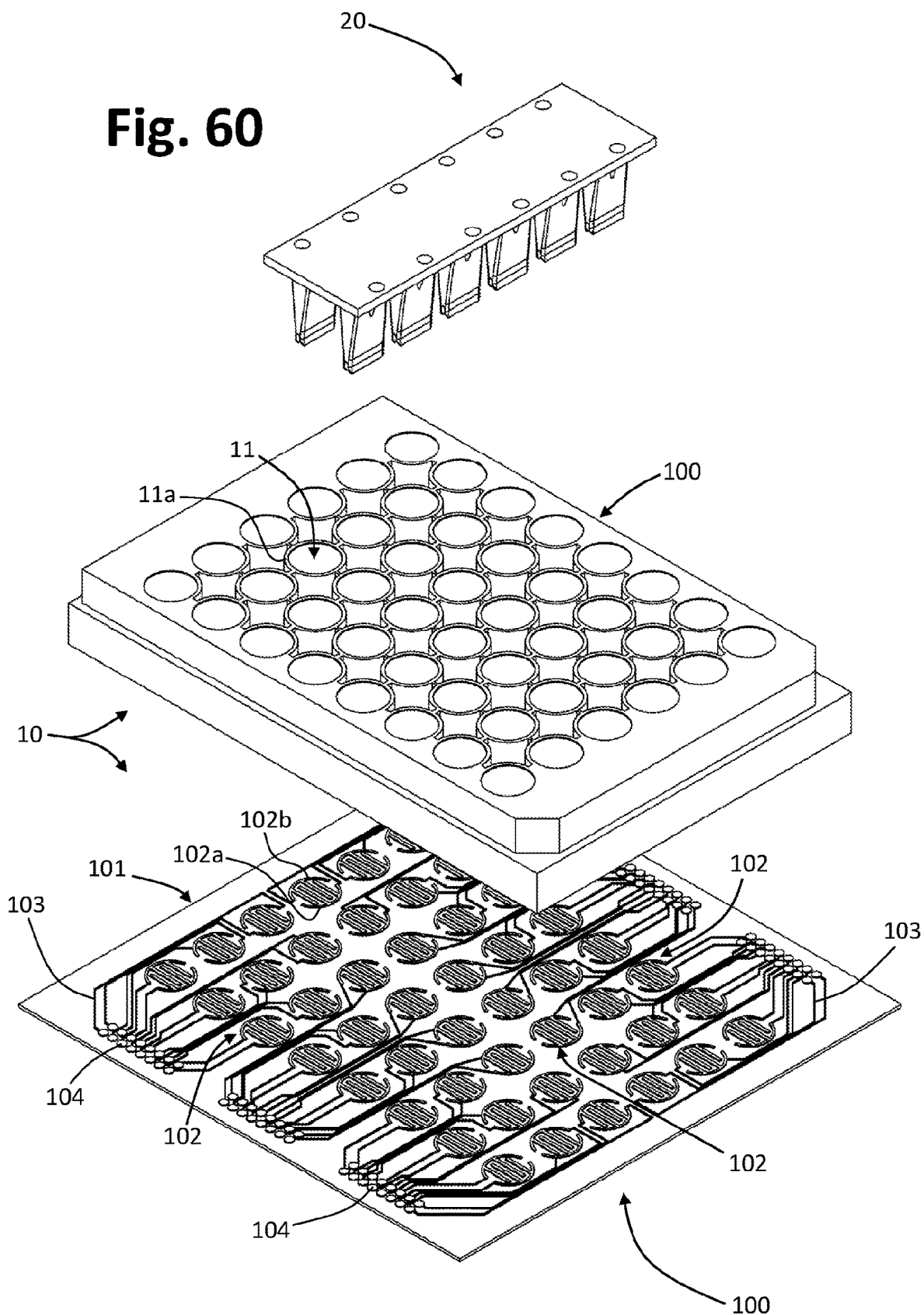
FIG. 60 is an exploded schematic view of a kit that uses a device according to FIGS. 55-59.

As highlighted in FIG. 60, in embodiments of this type, the structure of the multi-well plate 10 basically comprises an upper component 100, which is substantially configured as the plates 10 described previously, but does not define integrally a bottom wall of its own, and the lower component, designated by 101, which is applied in a fluid-tight way to the component 100 in order to form the bottom thereof, and hence the individual bottoms 11b of the various wells 11. The aforesaid lower component 101 is basically formed by a circuit support made of electrically insulating, preferably transparent, material, for example of a glass type.

Deposited, for example with a silk-screen printing technique, on the component or support 101 is an electrically conductive material so as to define a plurality of electrical elements, and in particular sets of electrodes 102, conductive paths 103, and pads or similar interfacing or electrical-connection elements 104, the electrodes 102 and/or conductive paths 103 preferably being made of a transparent material. Use of a transparent substrate and preferably also of transparent electrodes and paths enables optical detection of deposition of the cells and/or of the shape of the exclusion zone for cell growth EZ obtained by means of the exclusion reliefs 22 and/or of subsequent cell growth. This optical detection may be performed using a microscope, or a video camera, or some other detection device designed to carry out optical detection through the component 101, which here forms the bottom wall 10b of the wells.

The sets of electrodes 102 preferentially comprise at least two electrodes, two of which are designated by 102a and 102b, for example in FIG. 60, preferably shaped so as to have comb-fingered parts. Each set 102, i.e., the corresponding electrodes 102a, 102b, are shaped so as to extend in an area of the support 101 that can be circumscribed by the peripheral wall of a corresponding well 11. It will hence be appreciated that, in embodiments of this type, the bottom 11b of each well 11 is constituted by a respective region of the support 100, bearing a set of electrodes 102. The electrodes of the various sets 102 are connected via the paths 103 to respective connection elements 104, for electrical connection of the various sets of electrodes 102 to an external control and processing apparatus.

As has been said, the support 101 is fixed in a fluid-tight way to the upper component 100, and in particular at least at the lower end of the peripheral wall 11a of each well 11. It should be noted, in this regard, that the thickness (or height) of the components 102 and 103 deposited on the support 100 is very small (some nanometres or micrometres) and that fixing in a fluid-tight way can be performed with the aid of suitable biocompatible adhesives.

Figure 61:
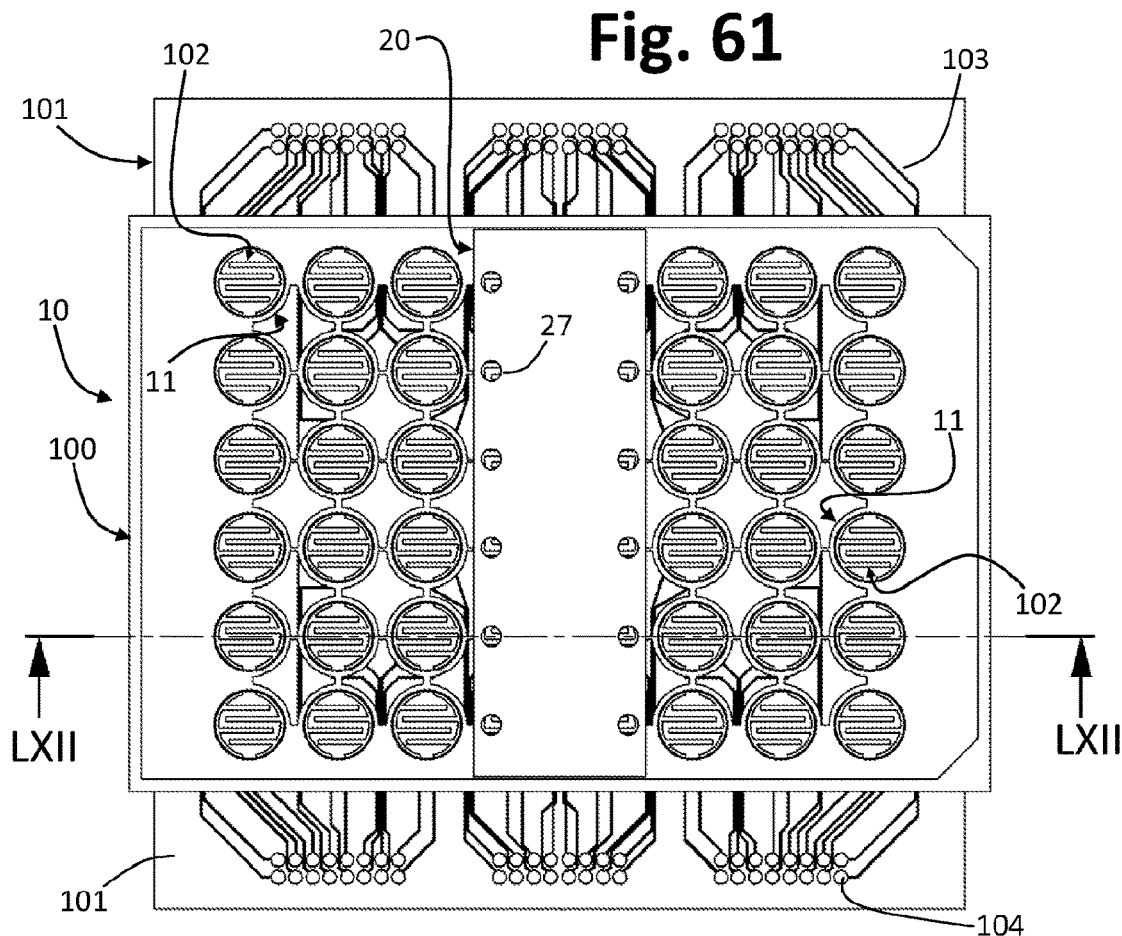
FIG. 61 is a schematic top plan view of the kit of FIG. 60.
Figure 62:
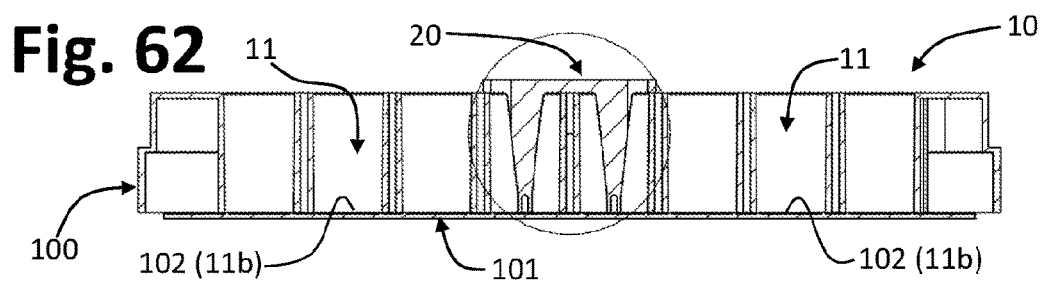
FIG. 62 is a schematic cross-sectional view according to the line LXII-LXII of FIG. 61.
Figure 63:
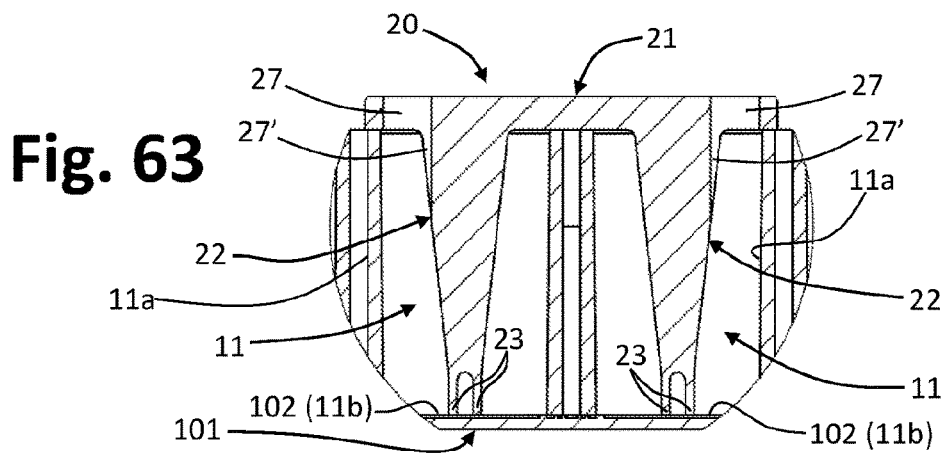
FIG. 63 illustrates the detail LXIII of FIG. 62 at a larger scale.
Figure 64:
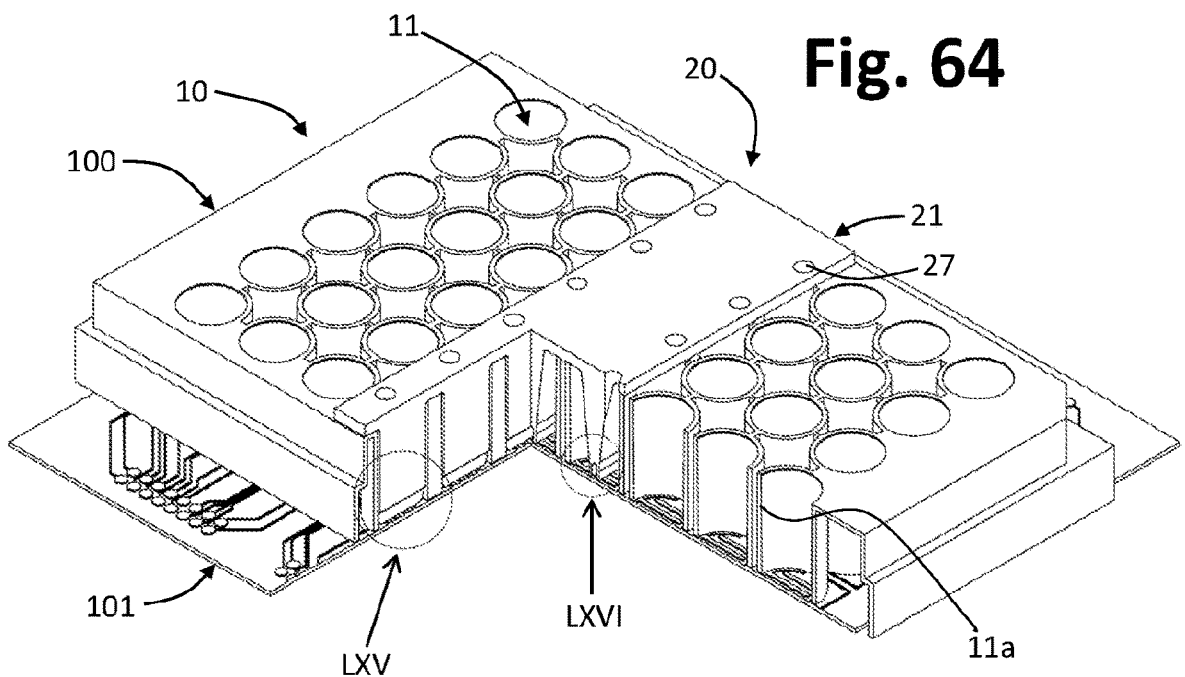
FIG. 64 is a sectioned perspective view of the kit of FIG. 60.
Figure 65:
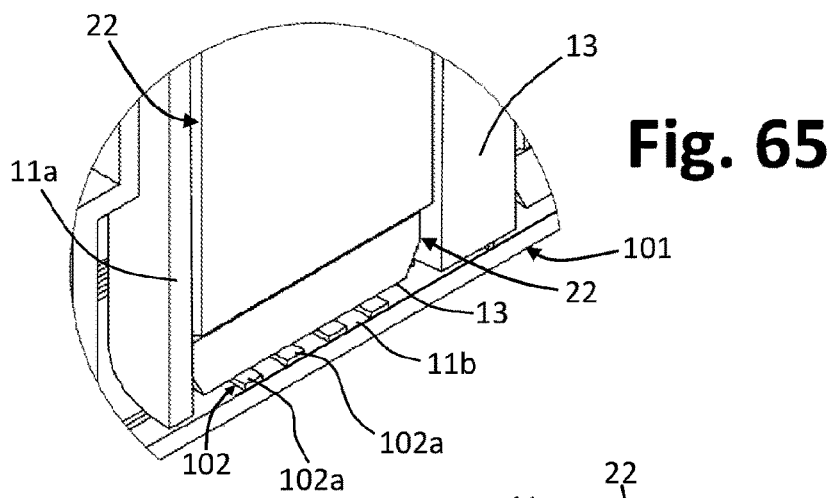
FIGS. 65 and 66 illustrate the details LXV and LXVI of FIG. 64 at a larger scale.
Figure 66:
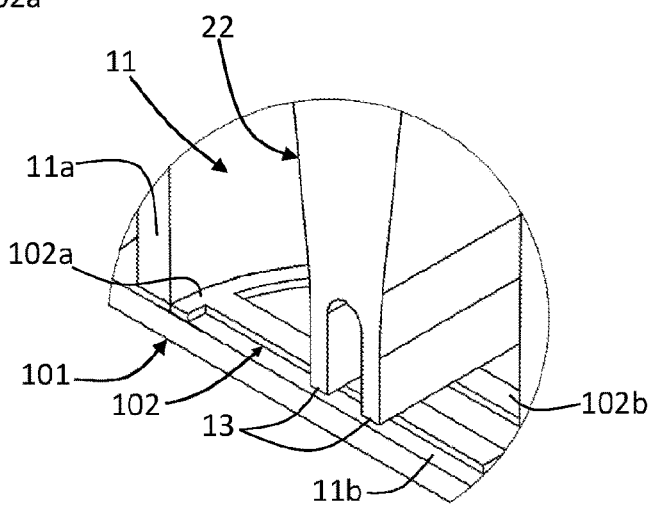

Hence, in the assembled condition, as may be seen, for example, in FIGS. 61 and 62, the support 101 forms the bottom of the multi-well plate 10, and thus the bottom 11b of each well 11 provided with a set of electrodes 102.

FIGS. 60-66 highlight, as has been said, the case of use of an insert 20 of the "double distal end" type 23, but this is not to be understood as in any way limiting given that, in a plate 10 with active bottom of the type exemplified, inserts 20 variously configured according to what has been described previously may be used. In any case, FIG. 63 clearly highlights how, in the case illustrated, the two ends 23 of the exclusion relief 22 represented rest elastically on the bottom 11b of the corresponding well 11, and hence in part on the electrodes of the corresponding set of electrodes 12 in order to enable definition of the cell-exclusion zones (see what has been described previously with reference to FIGS. 50-51). The condition of resting of the ends 23 of the reliefs 22 is moreover visible also in FIGS. 64-66, where the dimension of thickness (height) of the electrodes 120a, 102b has been enlarged for greater clarity of representation.

In use, after removal of the insert 20 and consequent creation of the exclusion zones in the various wells 11 (see, for reference, what has been described in relation to part b) of FIG. 51), the electrodes of the various sets of electrodes 102 may be used in order to detect the rate of proliferation and/or migration of the cells, up to complete closing of the corresponding exclusion zone or zones. For this purpose, as has been said, the various sets of electrodes 12 are connected, via the paths 103 and the contact elements 104, to a known equipment provided for the purpose.

As has already been explained, according to an inventive aspect, use of exclusion inserts with ends having an elongated or oblong shape, i.e., provision of exclusion zones having an elongated or oblong shape, requires a shorter time to obtain complete closing of the exclusion zones, in particular as compared with the exclusion zones of a circular shape according to the prior art, thereby enabling a greater rapidity of execution of laboratory tests.

According to a further inventive aspect, use of exclusion reliefs with two or more distal ends set alongside or parallel to one another, having an elongated or oblong shape makes it possible to obtain, in a well, corresponding distinct exclusion zones, the total area of which may also have dimensions similar to the area of a single circular exclusion zone according to the known art: however, in the case of the inventive aspect considered herein, also given the same areas referred to, a greater rapidity of execution of the laboratory tests is enabled for the reasons already referred to above.

Figure 67:
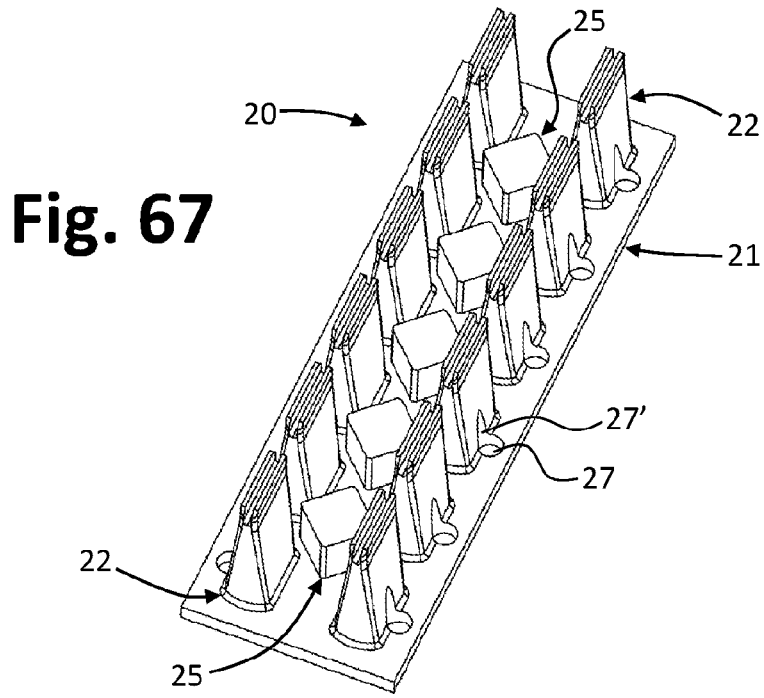
FIGS. 67, 68, and 69 are views similar to those of FIGS. 55, 56, and 58, of a device according to further possible embodiments of the invention.
Figure 68:
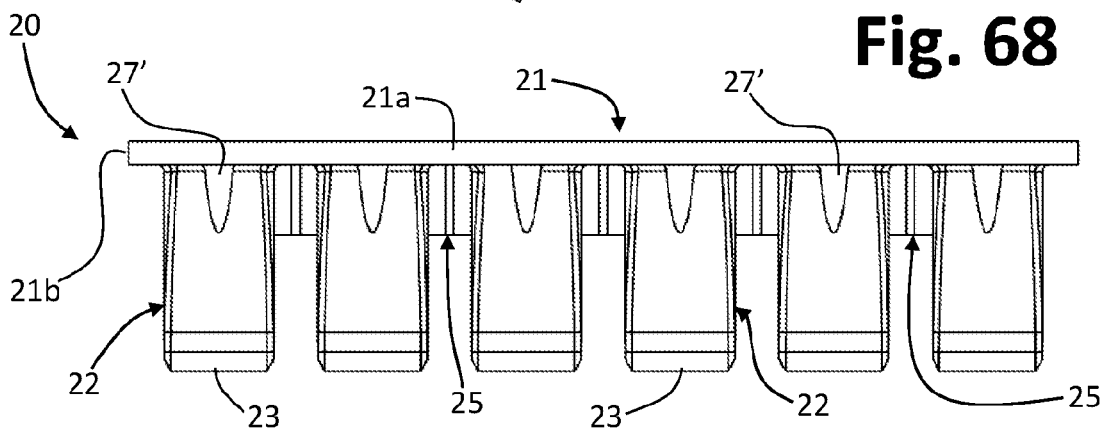
Figure 69:
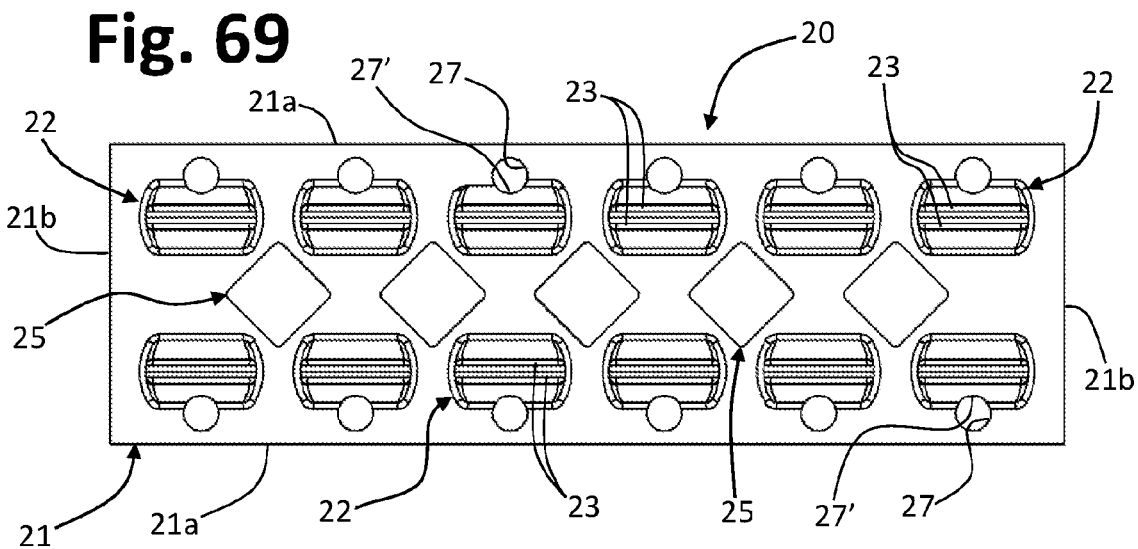

FIGS. 67, 68, and 69 illustrate further possible embodiments of the invention, where the insert 20 differs from that of FIGS. 55-59 basically as regards the shape of the constraint reliefs 25, which is here basically rhomboidal or square, for insertion with at least slight elastic interference into the gaps 12. For the rest, the insert and its mode of use are similar to those already described above. Also the insert 20 of FIGS. 67-69 may be variously sized, for example as illustrated in FIG. 25.

From the foregoing description, the characteristics of the present invention emerge clearly, as likewise do its advantages.

The exclusion devices or inserts according to the invention are simple and economically advantageous to produce in so far as they may be obtained via simple moulding operations.

The possibility of elastic deformation of the baseplate of the inserts facilitates the operations of coupling and removal of the inserts themselves to/from the corresponding multi-well culture plates. The possible elastic deformation of at least part of the exclusion device 20, in particular of the corresponding baseplate 21, enables insertion and/or extraction in succession or progressively of the reliefs 22, for example preventing mechanical stresses on the plate 10, which could occur in the case of a simultaneous extraction all the inserts 22 fitted in respective wells 11, where these stresses could damage the plate itself and/or alter the tests.

The above operations, as well as handling of the inserts, can be performed in a completely manual way, without the use of specific tools. The inserts described enable insertion (or removal), with a single operation, of a plurality of exclusion reliefs, all oriented in a homogeneous way, thus reducing the times for setting up an analysis.

The precision of positioning of the inserts and the corresponding maintenance in position can be guaranteed by the presence of the constraint reliefs, which are also elastically deformable and are preferably compatible with the gaps between the wells of standard culture plates or with other seats of the culture plate.

The constraint reliefs, when envisaged, also enable uniform detachment of the exclusion reliefs from the bottom surface of the corresponding wells, during manual extraction of the insert from the culture plate, for example, preventing possible movement of the reliefs still engaged in the corresponding well while adjacent reliefs are at least in part raised or extracted.

The inserts according to the invention may be suitable for use in combination with multi-well culture plates of a standard type, which typically have a structure resembling the one described herein and can be produced in various versions according to the type of culture plate (for example, inserts with 4, 6, 12, 24, 48, or 96 exclusion reliefs), it being possible, however, for them to be shaped for being used with culture plates of any other type.

According to variants (not represented), the elements used for coupling and/or positioning of the insert according to the invention with respect to a multi-well plate can have a shape different from the reliefs previously designated by 25 and/or be shaped and arranged in a perimetral position of the baseplate 21, for example for engaging with interference or in an elastic way at least part of the upper edge of the culture plate.

Obviously, it is possible to provide inserts 20 according to the invention with a number of exclusion reliefs 22 that have distal ends 23 differentiated with respect to one another in terms of shapes, dimensions, orientations, and number of ends 23 for each relief 22.

The invention claimed is:

1. A device for creating cell-exclusion zones in a test for studying cell migration or proliferation, the device comprising a multi-well cell-culture plate and a baseplate having a first major face projecting from which are a plurality of exclusion reliefs, each exclusion relief having at least one distal end configured for contact with a bottom of a respective well of the multi-well cell-culture plate, the baseplate being designed to be superimposed on the multi-well cell-culture plate and subsequently removed therefrom, wherein also projecting from said first major face are a plurality of constraint reliefs, each constraint relief being defined in a central position relative to four contiguous exclusion reliefs, wherein the baseplate, the plurality of exclusion reliefs and the plurality of constraint reliefs are defined at least in part by an elastic or flexible material, wherein when the baseplate is superimposed on the multi-well cell-culture plate:

the exclusion reliefs are inserted in corresponding wells of the multi-well cell-culture plate, with the at least one distal end of each exclusion relief which is elastically pressed on the bottom of the corresponding well; and each constraint relief is elastically coupled in a corresponding constraint seat of the multi-well cell-culture plate, to obtain removable fixing of the baseplate to the multi-well cell-culture plate and centring of the exclusion reliefs within the corresponding wells, and wherein during removal of the baseplate from the multi-well cell-culture plate, a tensile force exerted upwards on the baseplate at an edge thereof causes bending or elastic deformation of at least part of the baseplate and elastic uncoupling of the constraint reliefs from the corresponding constraint seats.

2. The device according to claim 1, wherein the baseplate and the plurality of exclusion reliefs are defined in a single body made of said elastic or flexible material.

3. The device according to claim 1, wherein:

the exclusion reliefs have a main section with at least two plane opposite walls; and/or each exclusion relief has two opposite major faces shaped so as to extend at least approximately parallel to one another at least in a distal end portion of the exclusion relief.

4. The device according to claim 1, wherein the at least one distal end has an elongated or oblong profile.

5. The device according to claim 1, wherein said at least one distal end of said each exclusion reliefs has a plurality of distal ends.

6. The device according to claim 1, wherein the baseplate has a plurality of recesses or through openings, each recess or through opening being defined in a lateral position relative to an exclusion relief of the plurality of exclusion reliefs, each recess or through opening being configured for enabling access to a well of the multi-well cell-culture plate in which the corresponding exclusion relief is inserted when the baseplate is superimposed to the multi-well cell-culture plate.

7. A kit for creating cell-exclusion zones comprising:
at one device for creating cell-exclusion zones according to claim 1;
wherein the multi-well cell-culture plate defines a plurality of parallel rows of wells, wherein each well has a peripheral wall and a bottom wall, the multi-well cell-culture plate also defining a plurality of constraint seats, each in a central position relative to four contiguous wells.

8. A method for creating cell-exclusion zones in a test for studying cell migration or proliferation, the method comprising the steps of:
(a) providing a multi-well cell-culture plate comprising:
a plurality of parallel rows of wells, each well having a peripheral wall and a bottom, and
a plurality of constraint seats, each in a central position relative to four contiguous wells,
(b) providing a baseplate for creating cell-exclusion zones (EZ) in the wells of the multi-well cell-culture plate, the baseplate having a first major face projecting from which are a plurality of exclusion reliefs in a plurality of parallel rows, each having at least one distal end configured for contact with the bottom of a respective well, and providing a plurality of constraint reliefs projecting from said first major face, each constraint relief being defined in a central position relative to four contiguous exclusion reliefs,
(c) superimposing the baseplate on the multi-well cell-culture plate, in such a way that the exclusion reliefs are inserted in corresponding wells of the multi-well cell-culture plate, with the at least one distal end of each exclusion relief elastically on the bottom of the corresponding well, and elastically pressing the at least one distal end of each exclusion relief on the bottom of the corresponding well, and elastically coupling each constraint relief in a corresponding constraint seat, to obtain removable fixing of the baseplate to the multi-well cell-culture plate and centring of the exclusion reliefs within the corresponding wells;
(d) introducing cells into a plurality of wells of the multi-well cell-culture plate in which respective exclusion reliefs of the baseplate are inserted;
(e) allowing the cells to stabilise at the bottom of each well, in such a way that the cells form at least one layer that coats the bottom of the corresponding well except for the area occupied by the at least one distal end of the corresponding exclusion relief; and
(f) removing the baseplate from the multi-well cell-culture plate, and exerting a tensile force upwards on the baseplate, at an edge thereof, thereby causing bending or elastic deformation of at least part of the baseplate as it is being moved away from the multi-well cell-culture plate, and elastic uncoupling of the constraint reliefs from the corresponding constraint seats,
the plurality of exclusion reliefs and the plurality of constraint reliefs comprising elastic or flexible material.

9. The device according to claim 1, wherein, the elastic or flexible material is an elastomer.

10. The device according to claim 3, wherein the exclusion reliefs have a main section with at least two plane opposite walls inclined with respect to one another at least in part in opposite directions.

11. The device according to claim 6, wherein the baseplate has, in positions corresponding to at least some exclusion reliefs, at least two through openings in lateral positions opposite relative to a respective exclusion relief.

* * * * *